United States Patent
Legangneux et al.

(10) Patent No.: US 11,944,602 B2
(45) Date of Patent: Apr. 2, 2024

(54) TREATMENT OF AUTOIMMUNE DISEASE IN A PATIENT RECEIVING ADDITIONALLY A BETA-BLOCKER

(71) Applicant: Novartis AG, Basel (CH)

(72) Inventors: Eric Legangneux, Levallois-Perret (FR); Alexandros Sagkriotis, Basel (CH); Pierre Jordaan, Bettingen (CH); Florine Polus, Basel (CH); Alan John Camm, London (GB); Shibadas Biswal, Nucleos North Tower (SG); Parasar Pal, Rangareddy (IN); Uday Kiran Veldandi, Rangareddy (IN); Atul Keshav Pawar, Navi Mumbai (IN); Vassilios Aslanis, Basel (CH); Kasra Shakeri-Nejad, Basel (CH)

(73) Assignee: NOVARTIS AG, Basel (CH)

(*) Notice: Subject to any disclaimer, the term of this patent is extended or adjusted under 35 U.S.C. 154(b) by 151 days.

(21) Appl. No.: 17/209,940

(22) Filed: Mar. 23, 2021

(65) Prior Publication Data
US 2022/0008385 A1  Jan. 13, 2022

Related U.S. Application Data

(63) Continuation of application No. 16/684,170, filed on Nov. 14, 2019, now abandoned, which is a (Continued)

(30) Foreign Application Priority Data

Feb. 26, 2015  (IN) .............................. 559/DEL/2015

(51) Int. Cl.
A61K 31/397 (2006.01)
A61K 9/20 (2006.01)
(Continued)

(52) U.S. Cl.
CPC .......... *A61K 31/397* (2013.01); *A61K 9/2018* (2013.01); *A61K 31/138* (2013.01); *A61K 45/06* (2013.01); *A61P 37/00* (2018.01)

(58) Field of Classification Search
CPC ...... A61K 31/397; A61K 31/138; A61P 37/00
See application file for complete search history.

(56) References Cited

U.S. PATENT DOCUMENTS 5,604,229 A  2/1997 Fujita et al.
6,121,329 A  9/2000 Fujii et al.
(Continued)

FOREIGN PATENT DOCUMENTS

CA  2521325 A1  10/2004
CN  103458877 A  12/2013
(Continued)

OTHER PUBLICATIONS

Selmaj et al. "Siponimod for patients with relapse-remitting multiple sclerosis(BOLD): an adaptive, dose-ranging, randomized phase 2 study," Lancet Neurol, Jun. 11, 2013, vol. 12, pp. 756-767 (Year: 2013).*

(Continued)

*Primary Examiner* — Shengjun Wang
(74) *Attorney, Agent, or Firm* — Adil R. Zhugralin

(57) ABSTRACT

The present invention relates to methods of treating autoimmune diseases with siponimod in patients receiving additionally a beta-blocker.

43 Claims, 4 Drawing Sheets

Study design

Related U.S. Application Data continuation of application No. 16/058,404, filed on Aug. 8, 2018, now abandoned, which is a continuation of application No. 15/552,886, filed as application No. PCT/IB2016/051004 on Feb. 24, 2016, now abandoned.

(51) Int. Cl.
*A61K 31/138* (2006.01)
*A61K 45/06* (2006.01)
*A61P 37/00* (2006.01)

(56) References Cited

U.S. PATENT DOCUMENTS

| | | |
|---|---|---|
| 8,492,441 B2 | 7/2013 | Legangneux |
| 2005/0014728 A1 | 1/2005 | Pan et al. |
| 2005/0090520 A1 | 4/2005 | Lindquist |
| 2006/0173052 A1 | 8/2006 | Rundfeldt et al. |
| 2006/0198884 A1 | 9/2006 | Yang et al. |
| 2012/0115840 A1 | 5/2012 | Ciszewski et al. |

FOREIGN PATENT DOCUMENTS

| | | |
|---|---|---|
| EP | 3047848 | 7/2016 |
| JP | 2008-150370 | 7/2008 |
| RU | 2296999 C2 | 4/2007 |
| WO | WO 2002/018395 | 3/2002 |
| WO | WO 2003/097028 A1 | 11/2003 |
| WO | WO 2004/103306 A2 | 12/2004 |
| WO | WO 2004/113330 A1 | 12/2004 |
| WO | WO 2005/000833 A1 | 1/2005 |
| WO | WO 2005/105146 A1 | 11/2005 |
| WO | WO 2006/058316 A1 | 6/2006 |
| WO | WO 2006/094705 A1 | 9/2006 |
| WO | WO 2007/021666 A2 | 2/2007 |
| WO | WO 2008/000419 A1 | 1/2008 |
| WO | WO 2008/072056 A1 | 6/2008 |
| WO | WO 2008/128739 A1 | 10/2008 |
| WO | WO 2008/135522 A1 | 11/2008 |
| WO | WO 2009/115954 A1 | 9/2009 |
| WO | WO 2010/010127 A1 | 1/2010 |
| WO | WO 2010/070083 A1 | 6/2010 |
| WO | WO 2010/071794 A1 | 6/2010 |
| WO | WO2010/072703 A1 | 7/2010 |
| WO | WO 2010/072703 A1 | 7/2010 |
| WO | WO 2010/075239 A1 | 7/2010 |
| WO | WO 2010/080409 A1 | 7/2010 |
| WO | WO 2010/080455 A1 | 7/2010 |
| WO | WO 2013/055833 A1 | 4/2013 |
| WO | WO 2014/161606 A1 | 10/2014 |

OTHER PUBLICATIONS

S Biswal: "Effects of siponimod (BAF312) alone and when combined with propranolol on absolute lymphocyte count decrease and recovery in healthy subjects", European Journal of Neurology, vol. 21, Suppl. 1, May 1, 2014, p. 452.

Biswal Shibadas et al: "Pharmacokinetic and pharmacodynamic interaction of siponimod (BAF312) and propranolol in healthy subjects", International Journal of Clinical Pharmacology and Therapeutics, vol. 53, No. 10, Oct. 1, 2015, pp. 855-865,.

Eric Legangneux et al: "Dose titration of BAF312 attenuates the initial heart rate reducing effect in healthy subjects", British Journal of Clinical Pharmacology, Jul. 1, 2012, pp. 831-841.

\* cited by examiner

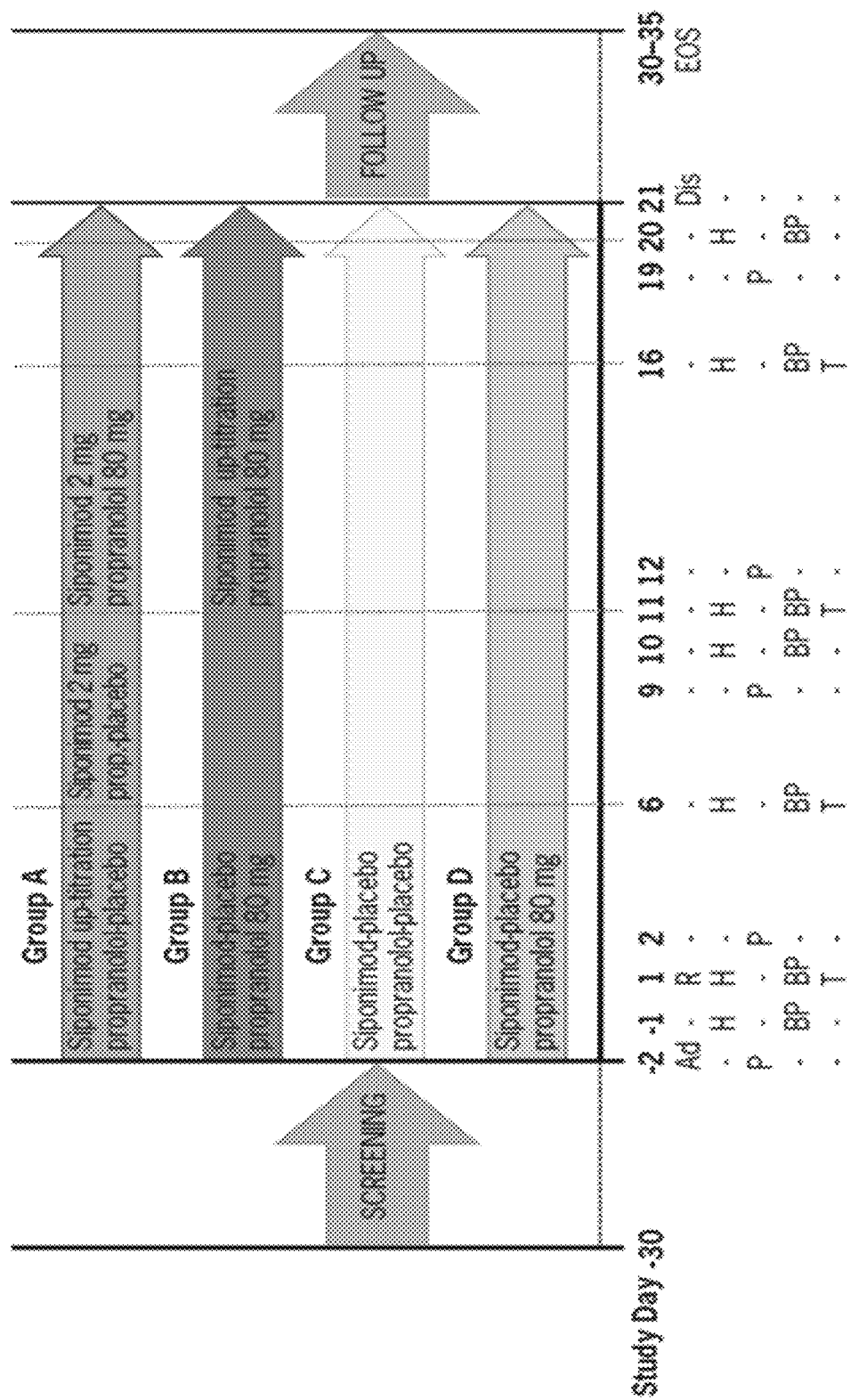
Figure 1: Study design

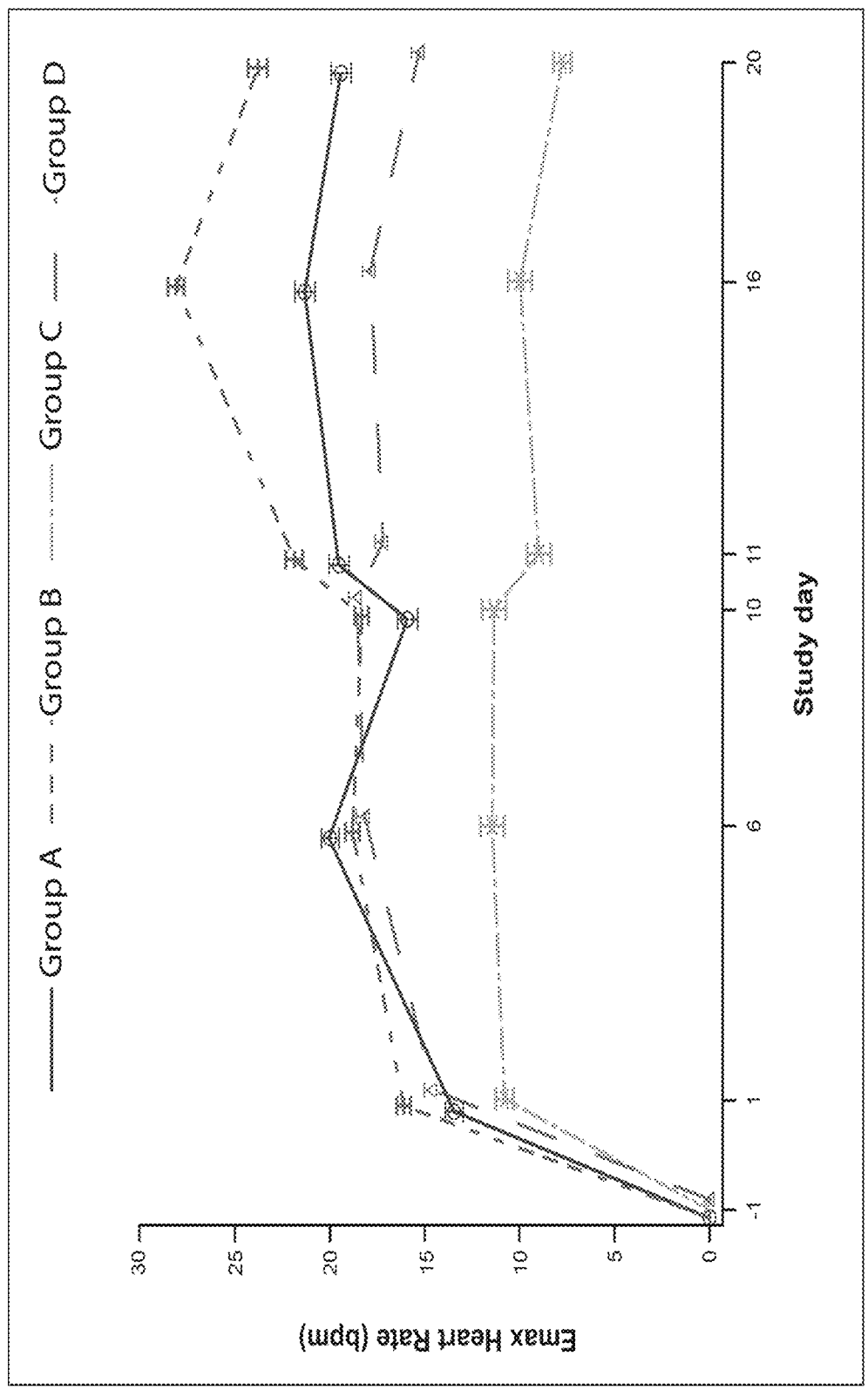
Figure 2: Emax heart rate by time and treatment group.

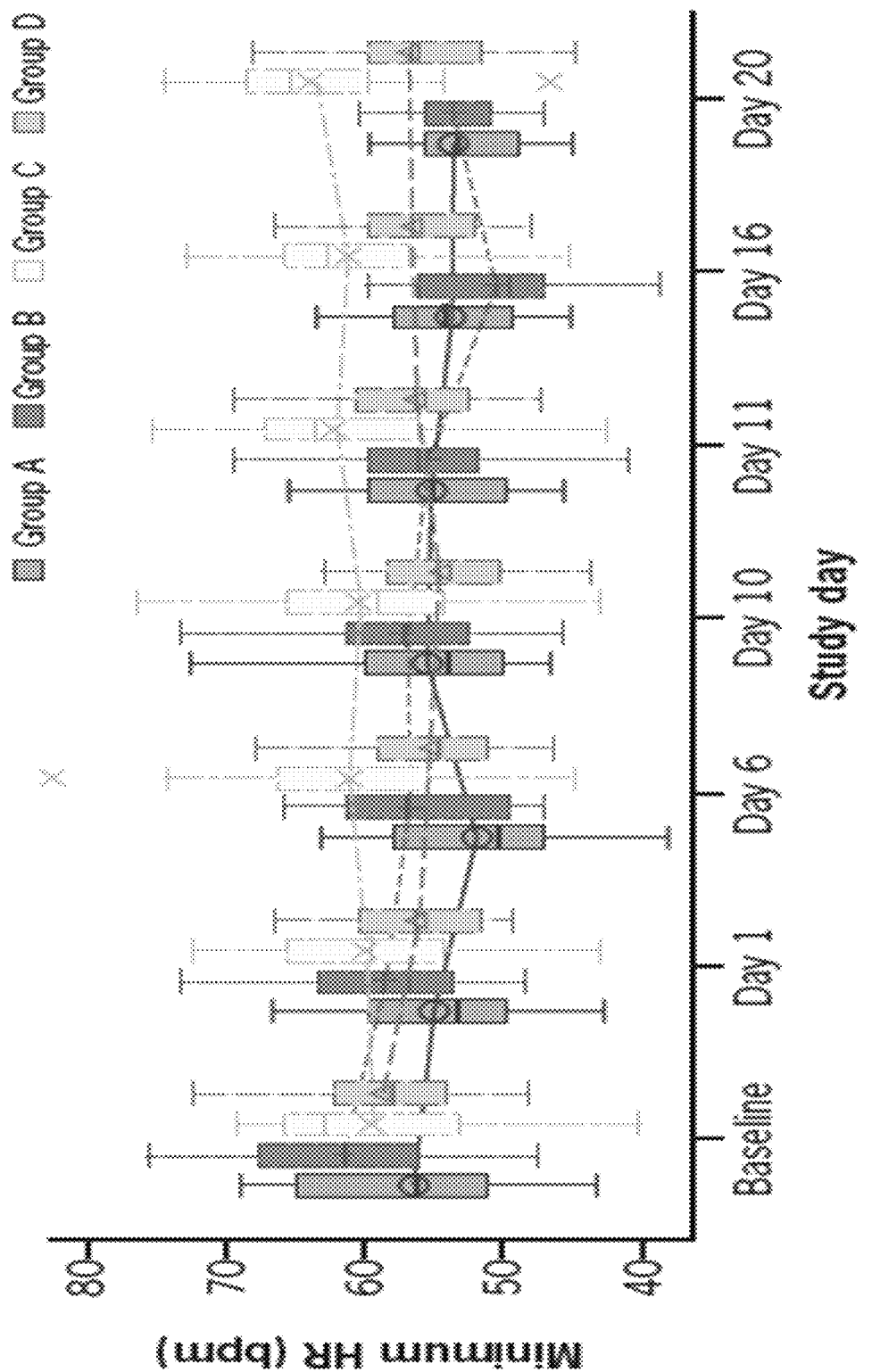
Figure 3: Minimum heart rate by time and treatment group

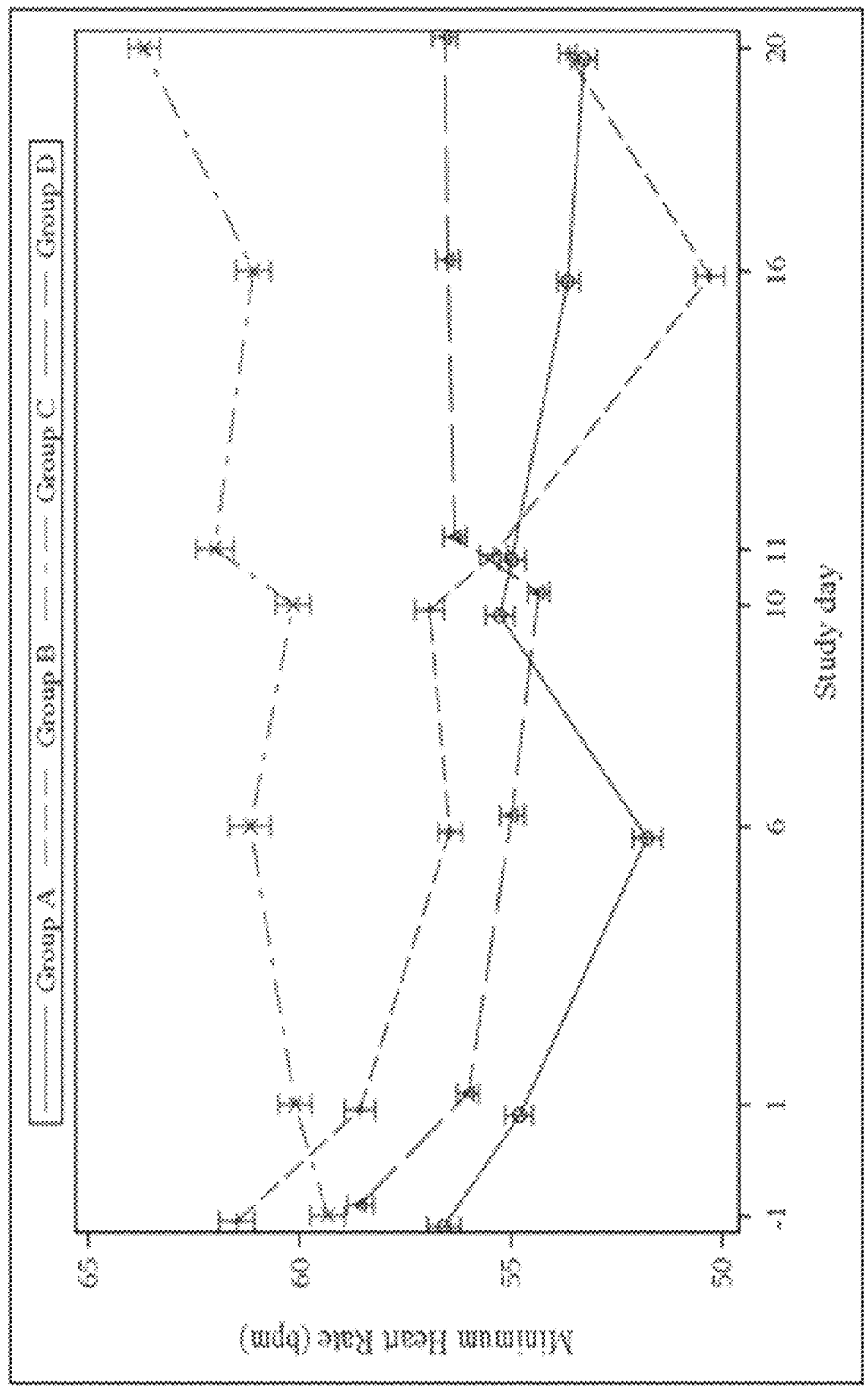
Figure 4: Minimum heart rate by time and treatment group.

TREATMENT OF AUTOIMMUNE DISEASE IN A PATIENT RECEIVING ADDITIONALLY A BETA-BLOCKER

FIELD OF THE INVENTION

The present invention relates to methods of treating autoimmune diseases with siponimod (BAF312) in patients receiving additionally a beta-blocker.

BACKGROUND

One of the mast common inflammatory, demyelinating diseases of the central nervous system (CNS) is multiple sclerosis (MS), in which the insulating covers of nerve cells in the brain and spinal cord are damaged. MS takes several forms, with new symptoms either occurring in isolated attacks (relapsing forms) or building up over time (progressive forms). Between attacks, symptoms may be completely in remission. However, as the disease progresses over time or relapses occur, permanent neurological problems result.

At the time of diagnosis, between 80% and 90% of MS patients have relapsing-remitting MS (RRMS). This form of MS is characterized by recurring relapses, i.e. acute episodes, of neurological symptoms. In around 80% of the patients with RRMS, this form then develops to secondary progressive MS (SPMS), around 19 years after disease onset. Progression proceeds with or without occasional relapses with minor remissions between relapses and is characterized symptomatically by continuous worsening of disability, independent of relapses.

Sphingosine-1-phosphate (S1P) receptors belong to a family of closely related, lipid-activated G-protein-coupled receptors. S1P1, S1P2, S1P3, 51P4, and S1P5 (also respectively termed EDG-1, EDG-5, EDG-3, EDG-6 and EDG-8) are identified as receptors specific for S1P. Certain S1P receptors are associated with diseases mediated by lymphocyte interactions, for example, in transplantation rejections, autoimmune diseases, e.g. MS and inflammatory myopathies, inflammatory diseases, infectious diseases and cancer. Hence, S1P receptor modulators, such as fingolimod and siponimod, are an interesting class of compounds for treating autoimmune diseases such as MS.

Fingolimod is well established in clinical practice for the treatment of relapsing forms of MS, e.g. RRMS.

Siponimod has achieved positive results in a clinical trial for the treatment of RRMS patients (see: Selmaj et al, Lancet Neurol, 2013, 12, 756-767) and is currently being investigated in an ongoing phase III study in patients with SPMS.

While S1P receptor modulators are interesting and mostly effective compounds for treating diseases e.g. mediated by lymphocyte interactions, they may produce negative chronotropic side effects at therapeutic doses, i.e. they may reduce the heart rate (bradycardia), as described in Cohen et al (N Engl. J Med 2010, 362, 402-415) and in Kappos et al (N Engl J Med 2010, 362, 387-401). Pronounced bradycardia may result in e.g. fatigue, weakness, dizziness and fainting, but may also be associated with bradyarrhythmia (e.g. AV blocks, AVB, and Sinus pauses, SP). While such bradycardia and its potential related side-effects might not be highly problematic for healthy patients, it might be critical for patients with a reduced clinical condition, e.g. patients with SPMS—as e.g. cardiovascular co-morbidities are more frequent in SPMS patients.

Beta-blockers, e.g. propranolol, are amongst the most commonly used medications for hypertension, angina pectoris, migraine, tremor, etc. and are known to also produce a negative chronotropic effect (i.e. bradycardia and bradyarrhythmia).

Patients with MS may have co-morbidities requiring beta-blocker therapy e.g. hypertension. A recent study calculated the prevalence of hypertension in MS patients to be 20.8%, i.e. similar to the prevalence of 22.5% in the general population (Marrie et al, Multiple Sclerosis Journal, 2012, 18(9), 1301-1319). Prevalence of hypertension increased with age of MS patients and was as high as 46.0% in MS patients being a ≥60 years old (vs. 55.5% for general population being a 60 years old). As MS patients develop SPMS only around 19 years after disease onset, prevalence of hypertension in SPMS patients will be significantly higher than the average value of 22.5% for general MS population.

In accordance with an expectation of additive effects between S1P modulators and beta-blockers on bradycardia/bradyarrhythmia, the fingolimod label discourages concomitant use. Furthermore, in the above mentioned clinical trial for the treatment of RRMS patients with siponimod patients requiring beta-blocker treatment have been excluded and concomitant use has been avoided (see: Selmaj et al, Lancet Neurol, 2013, 12, 756-767).

In clinical practice, there are two main scenarios where a concomitant use may be beneficial are conceivable: (1) a patient receiving a beta-blocker, e.g. a hypertensive patient, is diagnosed with an autoimmune disease, e.g. SPMS, for which S1P modulator treatment, e.g. siponimod treatment, would be an effective treatment; or (2) an autoimmune disease patient, e.g. a SPMS patient, receiving a S1P modulator, e.g. siponimod, is diagnosed with an indication for which a beta-blocker treatment would be an effective treatment, e.g. hypertension. However, in accordance with the teaching of the prior art, a physician would clearly be discouraged to consider treating such a patient with both drugs concomitantly although be may consider that both drugs would be the optimal treatment for both diseases individually.

Taking into account the high prevalence for e.g. hypertension in MS, especially in SPMS, avoiding concomitant use of S1P modulators and beta-blockers would lead to a significant number of patients not receiving an effective medication for the management of their disease states.

Hence, there is a need for an effective method for the treatment of autoimmune diseases, e.g. SPMS, in a patient in need of a combined administration of a S1P modulator and a beta-blocker.

SUMMARY OF THE INVENTION

Surprisingly it has been found that bradyarrhythmic effects are markedly less pronounced, i.e. considerably less than additive, when a beta-blocker is added to siponimod steady-state therapy, compared with siponimod addition to beta-blocker steady state therapy. These findings suggest that co-administration of a beta-blocker on top of siponimod has a better safety profile than co-administration of siponimod on top of a beta-blocker.

Based on their surprising finding that bradyarrhythmic effects are more pronounced when siponimod is added to a beta-blocker steady state therapy, the inventors have further found that for patients receiving a stable dose of beta-blocker, the resting heart-rate should be considered before introducing siponimod treatment. Namely, if the resting heart-rate is >50 bpm under chronic beta-blocker treatment, siponimod can be introduced. If on the other hand the resting heart rate is ≤50 bpm, then beta-blocker treatment should be interrupted until the baseline heart-rate is >50 bpm. Treatment with siponimod can then be initiated and treatment with beta-blocker can be re-initiated at a later point in time as described in detail below.

In accordance with a first aspect of the invention, there is provided a method of treating an autoimmune disease in a patient comprising
  a) administering to said patient an initial titration regimen of siponimod;
  b) administering to said patient 1-15 mg siponimod daily as a maintenance regimen; and
  c) introducing in said patient a beta-blocker treatment the earliest at the first day when said patient is receiving the dosage of the maintenance regimen;
wherein said initial titration regimen comprises administering siponimod at a dosage lower than the dosage of the maintenance regimen and then increasing the dosage stepwise up to the dosage of the maintenance regimen.

In accordance with a second aspect of the invention, there is provided a method of treating an autoimmune disease in a patient receiving a chronic beta-blocker treatment and having a resting heart rate of >50 bpm under said chronic beta-blocker treatment comprising introducing in said patient a siponimod treatment by
  a) administering to said patient an initial titration regimen of siponimod; and
  b) administering to said patient 1-15 mg siponimod daily as a maintenance regimen;
wherein said initial titration regimen comprises administering siponimod at a dosage lower than the dosage of the maintenance regimen and then increasing the dosage stepwise up to the dosage of the maintenance regimen.

In accordance with a third aspect of the invention, there is provided a method of treating an autoimmune disease in a patient receiving a chronic beta-blacker treatment and having a resting heart rate of ≤50 bpm under said chronic beta-blocker treatment comprising
  a) interrupting said chronic beta-blocker treatment in said patient until the baseline heart-rate is ≤50 bpm;
  b) initiating in said patient a siponimod treatment by
    b1) administering to said patient an initial titration regimen of siponimod; and
    b2) administering to said patient 1-15 mg siponimod daily as a maintenance regimen; and
  c) re-initiating in said patient a beta-blocker treatment the earliest at the first day when said patient is receiving the dosage of the maintenance regimen;
wherein said initial titration regimen comprises administering siponimod at a dosage lower than the dosage of the maintenance regimen and then increasing the dosage stepwise up to the dosage of the maintenance regimen.

BRIEF DESCRIPTION OF THE FIGURES

FIG. 1: Design of study on cardiovascular effects of combined administration of siponimod and propranolol in healthy volunteers (example 2). Key: Ad=admission to clinic for in-patient stay; BP=blood pressure profile; Dis=discharge from clinic; H=Holter assessment; P=pulmonary function test (spirometry); R=randomization; T=telemetry (cardiac monitoring); EOS=end of study.

FIG. 2: $E_{max}$ heart rate by time and treatment group as assessed in example 2. Group A=propranolol at siponimod steady state; group B=siponimod at propranolol steady state; group C=placebo; group D=propranolol (see also FIG. 1). Time Interval: 0-24 h. The median for each treatment is represented by circle (Group A), plus (Group B), cross (Group C) and triangle (Group D).

FIG. 3: Minimum heart rate by time and treatment group as assessed in example 2. Group A=propranolol at siponimod steady state; group B=siponimod at propranolol steady state; group C=placebo; group D=propranolol (see also FIG. 1). Time interval: 0-24 h. The median for each treatment is represented by circle (Group A), plus (Group 8), cross (Group C) and triangle (Group D) within the box. The upper (lower) edge of the box represents the 75th (25th) percentile. A whisker is drawn from the upper (lower) edge of the box to the largest (smallest) value within 1.5× interquartile range above (below) the edge of the box, and the values outside the whiskers are identified by the respective symbols.

FIG. 4: Minimum heart rate by time and treatment group as assessed in example 2. Group A=propranolol at siponimod steady state; group 8=siponimod at propranolol steady state; group C=placebo; group D=propranolol (see also FIG. 1). Time interval: 0-24 h. The median for each treatment is represented by circle (Group A), plus (Group B), cross (Group C) and triangle (Group D).

DETAILED DESCRIPTION OF THE INVENTION

For the avoidance of doubt, it is hereby stated that the information disclosed earlier in this specification under the heading "Background" is relevant to the invention and is to be read as part of the disclosure of the invention.

Throughout the description and claims of this specification, the words "comprise" and "contain" and variations of them mean "including but not limited to", and they are not intended to (and do not) exclude other moieties, additives, components, integers or steps.

Throughout the description and claims of this specification, the singular encompasses the plural unless the context otherwise requires. In particular, where the indefinite article is used, the specification (which term encompasses both the description and the claims) is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least same of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

Siponimod

"Siponimod" as used herein is understood to comprise the compound of formula (1)

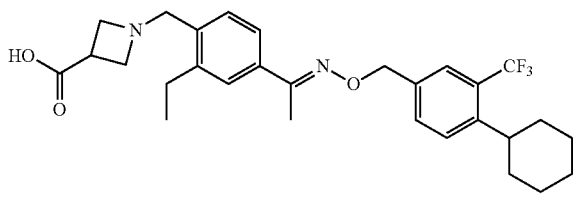

(I)

as well as the pharmaceutically acceptable salts, polymorphs, solvates and/or hydrates thereof. Siponimod as used herein has the IUPAC-name 1-{4-[1-((E)-4-cyclohexyl-3-trifluoromethyl-benzyloxyimino)-ethyl]-2-ethyl-benzyl}-azetidine-3-carboxylic acid (BAF312).

In a preferred embodiment of the invention, siponimod is present in the form of siponimod free base or siponimod salt. Examples of pharmaceutically acceptable salts of siponimod include salts with inorganic acids, such as hydrochloride, hydrobromide and sulfate, salts with organic acids, such as acetate, fumarate, hemifumarate, maleate, benzoate, citrate, malate, methanesulfonate and benzenesulfonate salts, or, when appropriate, salts with metals such as sodium, potassium, calcium and aluminium, salts with amines, such as triethylamine and salts with dibasic amino acids, such as lysine. In a preferred embodiment siponimod is in the hemifumarate salt form.

In one embodiment of the invention, siponimod can be provided in an amorphous form or crystalline form, preferably in a crystalline form.

The term "crystalline" can be used in the context of this invention to describe the state of a solid substance, whose constituent atoms, molecules, or ions are arranged in an ordered pattern extending in all three spatial dimensions.

The siponimod as used in the context of this invention may consist of purely crystalline siponimod. Alternatively, it may also contain small amounts of non-crystalline siponimod components. In an embodiment of the invention the siponimod contained in the administered dosage form(s) can be 85 to 99.999%, more preferably 90 to 99.99%, most preferably 95 to 99.9% by weight crystalline siponimod.

Generally, siponimod as used in the context of this invention can be used in particulate form. The siponimod can preferably have an average particle size X90 of 10 to 100 µm, more preferably 15 to 80 µm, most preferably 30 to 70 µm.

The particle size X90, which is also denoted as X90 value of the integral volume distribution, is defined in the context of this invention as the particle diameter at which 90 percent by volume of the particles have a smaller diameter than the diameter which corresponds to the X90 value. Likewise, 10 percent by volume of the particles have a larger diameter than the X90 value. The X10 and X50 values are defined accordingly.

Further, the siponimod can preferably have an average particle size X50 of 1 to 25 µm, more preferably 2 to 22 µm, even more preferably 4 to 20 µm, especially 5 to 17 µm.

Yet further, the siponimod can preferably have a particle size X10 of 0.5 to 5 µm, more preferably 1 to 4 µm, even more preferably 1.2 to 3 µm, especially preferably 1.5 to 2.7 µm.

In a preferred embodiment the ratio X90/X50 can be 1.0 to 100, preferably 1.2 to 10, more preferably 2.5 to 4.0. In a preferred embodiment, the ratio X50/X10 can be 1.1 to 10, preferably 1.2 to 5, more preferably 2.5 to 4.0.

The particle size distribution by volume can be measured using laser diffractometry. In particular, it can be measured using the Sympatec Helos device (from Sympatec GmbH, Germany) using the Cuvette dispersion device. To make the measurement, a stock dispersion was prepared by mixing the drug substance with a dispersing aid (Octastat 5000 (Octel corp)) using a vortex until a smooth and homogeneous paste was formed. The paste was then diluted and mixed to a final volume of 3 to 6 ml using white spirit. The optical concentration of the final solution was kept below 5%. The percentage values were calculated from the mean cumulative volume size curve by the software of the Sympatec instrument. Preferably, the Fraunhofer method is used for calculation purposes.

Dosage Forms Comprising Siponimod

In one embodiment, the dosage form of the siponimod maintenance regimen according to the present invention is an immediate release dosage form. In a preferred embodiment of the invention, the dosage form of both the siponimod maintenance regimen and the siponimod titration regimen is an immediate release dosage form.

In one embodiment, the maintenance regimen of siponimod according to the invention comprises administering an immediate release dosage form of siponimod containing 1-15 mg siponimod, preferably 1-10 mg siponimod, more preferably 1-5 mg siponimod, most preferably 1-2 mg siponimod, based on the amount of siponimod in form of the free base. In a preferred embodiment, the siponimod immediate release dosage form of the maintenance regimen contains 2 mg of siponimod. In another preferred embodiment, the siponimod immediate release dosage form of the maintenance regimen contains 1 mg of siponimod.

Since siponimod can be present in the form of a salt (vide supra), the amount of the respective salt former (e.g. the respective acid) has to be added accordingly. Similar considerations apply for the dosage forms of both the titration regimen and the maintenance regimen. As an example, in a titration regimen comprising administering 0.25 mg siponimod at day 1, 0.25 mg siponimod at day 2, 0.5 mg siponimod at day 3, 0.75 mg siponimod at day 4, 1.25 mg siponimod at day 5, and 2 mg siponimod at day 6, each amount refers to the amount of siponimod in free form.

Preferably an immediate release dosage form is administered in the maintenance regimen as well as in the titration regimen. Generally, the term "immediate release dosage form" stands for a dosage form with an in-vitro release profile of the dosage form according to USP app. II (paddle, 500 mL for the 0.25 mg dosage strength, 900 mL for the 0.5, 1 and 2 mg dosage strengths, phosphate buffer+0.1% (m/v) Tween 80, 60 rpm±2 rpm, 37° C.±0.5° C.) wherein after 30 minutes preferably a content release of at least 80% is achieved, preferably more than 90%, more preferred of more than 95%. The release can be up to 100%.

Generally, the term "immediate release dosage form" stands for a dosage form with a release profile of the dosage form according to USP app. II (paddle, 900 ml, phosphate buffer+0.1% (m/v) Tween 80, 60 rpm, 37° C.) wherein after 30 minutes preferably a content release of at least 80% is achieved, preferably more than 90%, especially more than 95%, or a bioequivalent dosage form to said dosage form.

Tween 80 has the name polyoxyethylene(20) sorbitan monooleate of the formula

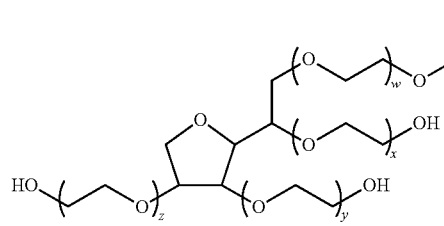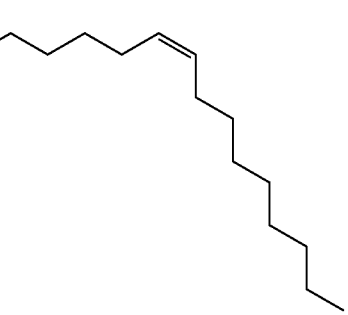

w + x + y + z = 20 and preferably has a density at 25° C. of around 1.06-1.09 g/mL, a viscosity at 25° C. of 300-500 mPa·s and a HLB-value (hydrophilic-lipophilic balance value) of 15.0, determined by the Griffin's method.

In the context of the invention it is understood that a dosage form being a bioequivalent dosage form to a dosage form which is described in Example 1 is an immediate release dosage form.

Generally, the term "bioequivalent dosage form" stands for a dosage form which fulfills the standard of the FDA or EMA with respect to another dosage form, e.g. as described in "FDA Guidance for Industry Bioavailability and Bioequivalence Studies for Orally Administered Drug Products—General Considerations" from 2003 or in "EMEA Note for Guidance on the Investigation of Bioavailability and Bioequivalence Bioequivalence" from 2000. According to these recommendations, the parameters and the corresponding 90% confidence intervals should lie within a range of acceptance of 80 to 125% of the reference preparation. In order to establish bioequivalence, it is necessary for 9 out of 10 of the pharmacokinetic measurement values of the test product to lie within this range of acceptance. Parameters relevant for bioequivalence according to those standards are Cmax and AUClast.

In one embodiment of the invention, the dosage form of siponimod is an oral solid dosage form. In one embodiment of the invention, the dosage form of siponimod is preferably a tablet. Alternatively, the dosage form of the invention could be a capsule.

The immediate release dosage form as used in the present invention can be formed by providing siponimod as described above and by blending siponimod with at least one pharmaceutical excipient. Typical pharmaceutical excipients comprise lubricants, glidants, fillers, disintegrants, moisture protecting agents and binders.

Fillers generally are substances suitable to add volume and/or mass to a drug substance, thereby facilitating precise metering and handling thereof in the preparation of dosage forms. Fillers typically also fill out the size of a tablet or capsule, making it practical to produce and convenient for the consumer to use.

Suitable fillers are plant cellulose (pure plant filler), hydroxypropyl cellulose, calcium phosphate, calcium hydrogen phosphate, calcium dihydrogen phosphate, calcium carbonate, magnesium carbonate, magnesium aluminosilicates, sugar alcohols, such as mannitol, maltitol, isomalt, sorbitol, xylitol, threitol and erythritol, a triglyceride, such as hydrogenated vegetable oil, mucilage such as carrageenan, agar and pectin, a monosaccharide such as arabinose, xylose, glucose, mannose, galactose, a disaccharide, such as isomaltose, maltose, lactose, sucrose, an oligosaccharide, such as raffinose, oligofructose, cyclodextrins, maltodextrin, a polysaccharide, such as starch, such as corn starch, glycogen and cellulose, such as microcrystalline cellulose, and mixtures thereof. Preferably, microcrystalline cellulose and lactose can be used as fillers.

Generally, the dosage form as used in the context of the present invention can comprise 0 to 90 wt.-% fillers, preferably 20 to 90 wt.-%, more preferably 30 to 80 wt.-%, based on the total weight of the dosage form.

Lubricants are generally substances suitable to reduce sliding friction. In particular, the intention is to reduce the sliding friction found during tablet pressing between the punch moving up and down in the die and the die wall, on the one hand, and between the edge of the tablet and the die wall, on the other hand. Suitable lubricants are, for example, stearic acid, adipic acid, sodium stearyl fumarate and/or glyceryl behenate.

Generally, the dosage form as used in the context of the present invention can comprise 0 to 10 wt.-% lubricants, preferably 0.01 to 8 wt.-%, more preferably 0.1 to 5 wt.-%, based on the total weight of the dosage form.

Binders are substances that ensure that granules or tablets can be formed with the required mechanical strength. Binders can be, for example, saccharose, gelatine, polyvinylpyrrolidone, starch, cellulose derivatives such as hydroxylpropyl cellulose, hydroxyethyl cellulose, hydroxypropyl methylcellulose (HPMC). Preferably, polyvinylpyrrolidone can be used as binder.

Generally, the dosage form as used in the context of the present invention can comprise 0 to 30 wt.-% binders, preferably 1 to 15 wt.-%, more preferably 2 to 10 wt.-%, based on the total weight of the dosage form.

Glidants can be used to improve the flowability. A preferred glidant is colloidal silica.

Generally, the dosage form as used in the context of the present invention can comprise 0 to 10 wt.-% glidants, preferably 0.1 to 5 wt.-%, more preferably 1 to 3 wt.-%, based on the total weight of the dosage form.

Disintegrants are substances which can enhance the ability of the intermediate to break into smaller fragments when in contact with a liquid, preferably water. Preferred disintegrants are guar galactomannan, sodium carboxymethyl starch (croscarmellose sodium), cross-linked polyvinylpyrrolidone (crospovidone), sodium carboxymethyl glycolate, sodium bicarbonate or mixtures thereof. Preferably croscarmellose and crospovidone can be used.

Generally, the dosage form as used in the context of the present invention can comprise 0 to 20 wt.-% disintegrants, preferably 1 to 12 wt.-%, more preferably 2 to 8 wt.-%, based on the total weight of the dosage form.

In a preferred embodiment of the invention, the immediate release dosage form comprises a moisture protective agent. The moisture protective agent is a substance suitable to protect the siponimod particles from moisture during the dosage form formation process and/or storage.

In one embodiment, the moisture protective agent is selected from hydrogenated vegetable oil, castor oil, palmitoyl stearate, glyceryl palmitostearate and glyceryl behenate. Preferably, glyceryl behenate is used as moisture protective agent. The moisture protective agent can also have lubricating properties. In case a moisture protective agent is used it is preferred that the dosage form does not contain any additional lubricants.

Generally, the dosage form as used in the context of the present invention can comprise 0 to 20 wt.-% moisture protective agent, preferably 0.1 to 12 wt.-%, more preferably 1 to 8 wt.-%, based on the total weight of the dosage form.

In a preferred embodiment, a dosage form as used in the context of the present invention comprises
  0.1 to 10 wt. %, preferably 0.2 to 5 wt. % siponimod,
  0 to 10 wt. %, preferably 0.2 to 6 wt. % moisture protective agent,
  0 to 15 wt. %, preferably 1 to 8 wt. % disintegrant,
  0 to 15 wt. %, optionally 1 to 8 wt. % binder,
  0 to 99.9 wt. %, preferably 50 to 90 wt. % filler, and
  0 to 10 wt. %, preferably 0.2 to 5 wt. % glidant.

In a preferred embodiment, a dosage form as used in the context of the present invention, preferably for use in the maintenance regimen comprises
  2 mg siponimod,
  0 to 15 mg, preferably 1 to 8 mg moisture protective agent,
  0 to 25 mg, preferably 0.5 to 15 mg disintegrant,
  15 to 250 mg, preferably 30 to 85 mg filler,
  0 to 50 mg, optionally 5 to 20 mg binder, and
  0 to 20 mg glidant, preferably 1 to 10 mg glidant.

In a preferred embodiment, a dosage form as used in the context of the present invention, preferably for use in the maintenance regimen comprises
  1 mg siponimod,
  0 to 15 mg, preferably 1 to 8 mg moisture protective agent,
  0 to 25 mg, preferably 0.5 to 15 mg disintegrant,
  15 to 250 mg, preferably 30 to 85 mg filler,
  0 to 50 mg, optionally 5 to 20 mg binder, and
  0 to 20 mg glidant, preferably 1 to 10 mg glidant.

In a preferred embodiment, a dosage form as used in the context of the present invention, preferably for use in the titration regimen comprises
  0.25 mg, 0.5 mg, 0.75 mg or 1 mg siponimod,
  0 to 15 mg, preferably 1 to 8 mg moisture protective agent,
  0 to 25 mg, preferably 0.5 to 15 mg disintegrant,
  15 to 250 mg, preferably 30 to 85 mg filler,
  0 to 50 mg, optionally 5 to 20 mg binder, and
  0 to 20 mg glidant, preferably 1 to 10 mg glidant.

The above-mentioned mixtures of siponimod with the at least one pharmaceutical excipient can be transformed into a dosage form, e.g. a capsule or a tablet, preferably a tablet.

The dosage form can be formed by direct compression. Hence, the above blending mixtures can be compressed into tablets.

Alternatively, the dosage form can be formed by dry granulation. Dry granulation involves the steps of dry powder blending, initial compaction (slugging or roller compaction), milling, addition of extragranular excipients and lubrication before compaction or capsule filling.

Further, if the dosage form is a tablet, the tablet can be film-coated. For this purpose, standard methods of film coating tablets may be employed. The above-mentioned amounts of siponimod and excipients, however, relate to the uncoated tablet.

For film coating, macromolecular substances are preferably used, such as modified celluloses, polymethacrylates, polyvinylpyrrolidone, polyvinyl acetate phthalate and/or shellac. In an embodiment the coating can have a thickness of 2 to 80 μm, more preferably 5 to 50 μm.

Release Profiles of Dosage Forms Comprising Siponimod

The preferred dosage forms have been described above. In a further preferred embodiment, a single 2 mg siponimod dosage form is administered as a maintenance regimen, leading in-vivo to a Cmax of 10 to 20 ng/ml, preferably 14.0 to 17.0 ng/ml, more preferably 14.5 to 16.5 ng/ml, still more preferably 15.0 to 16.0 ng/ml, and to a AUClast of 300 to 700 h·ng/ml, preferably 500 to 560 h·ng/ml, more preferably 510 to 550 h·ng/ml, still more preferably 520 to 540 h·ng/ml.

"Cmax" means the peak concentration of siponimod in the plasma, e.g. determined as described below. "AUClast" describes siponimod bioavailability and is measured by calculating the area under curve (AUC) of the plasma drug concentration time profile from time zero to the time of the last quantifiable concentration. AUClast can be determined as described below.

In a further preferred embodiment, a single 2 mg siponimod dosage form is administered as a maintenance regimen, the in-vivo AUC-time profile from time zero to infinity (AUCinf) of said dosage form being 350 to 750 h·ng/ml, preferably 520 to 600 h·ng/ml, more preferably 540 to 580 h·ng/ml, still more preferably 550 to 570 h·ng/ml.

In a further preferred embodiment, a single 2 mg siponimod dosage form is administered as a maintenance regimen, leading in-vivo to a Tmax of 3 to 8 h, preferably 3 to 7 h, more preferably 3 to 6 h, most preferably 3 to 5 h.

"Tmax" means the time from administration to reach Cmax.

The Cmax, AUClast, AUCInf and Tmax values typically can be determined in vivo in healthy subjects, aged 20 to 40 years. The subjects typically have maximal ±10% divergence from the ideal weight, in order to minimize a strong fluctuation of the distribution volume. Ideally, the administration of the medicament occurs on an empty stomach. The type and amount of the administration liquid is identical for every administration and for every subject. Blood samples are taken at the initial phase with a higher frequency than at a later stage, in order to increase the accuracy of the measurement.

The AUC values are calculated after one administration, preferably using the Trapezoidal Rule as is generally known in the art.

In a further preferred embodiment, the titration regimen comprises administering a 0.25 mg siponimod dosage form, said administration leading in-vivo to a Cmax of 1.3 to 2.6 ng/ml, preferably 1.5 to 2.4 ng/ml, more preferably 1.7 to 2.2 ng/ml, still more preferably 1.9 to 2.0 ng/ml, and to a AUClast of 45 to 90 h·ng/ml, preferably 50 to 80 h·ng/ml, more preferably 55 to 75 h·ng/ml, still more preferably 60 to 70 h·ng/ml.

In another preferred embodiment, the titration regimen comprises administering a 0.25 mg siponimod dosage form, the in-vivo AUC-time profile from time zero to infinity (AUCinf) of said dosage form being 47 to 95 h·ng/ml, preferably 55 to 85 h·ng/ml, more preferably 60 to 80 h·ng/ml, still more preferably 65 to 75 h·ng/ml.

In yet a further preferred embodiment of the invention, the titration regimen comprises administering a 0.25 mg siponimod dosage form, said administration leading in-vivo to a Tmax of 3 to 8 h, preferably 3 to 7 h, more preferably 3 to 6 h, most preferably 3 to 5 h.

In a further preferred embodiment, the titration regimen comprises administering a 0.5 mg siponimod dosage form, said administration leading in-vivo to a Cmax of 2.6 to 5.2 ng/ml, preferably 3.0 to 4.8 ng/ml, more preferably 3.4 to 4.4 ng/ml, still more preferably 3.7 to 4.0 ng/ml, and to a AUClast of 90 to 180 h·ng/ml, preferably 100 to 160 h·ng/ml, more preferably 110 to 150 h·ng/ml, still more preferably 120 to 140 h·ng/ml.

In a further preferred embodiment, the titration regimen comprises administering a 0.5 mg siponimod dosage form, the in-vivo AUC-time profile from time zero to infinity (AUCInf) of said dosage form being 95 to 190 h·ng/ml, preferably 110 to 170 h·ng/ml, more preferably 120 to 160 h·ng/ml, still more preferably 130 to 150 h·ng/ml.

In a further preferred embodiment of the invention, the titration regimen comprises administering a 0.5 mg siponimod dosage form, said administration leading in-vivo to a Tmax of 3 to 8 h, preferably 3 to 7 h, more preferably 3 to 6 h, most preferably 3 to 5 h.

In a further preferred embodiment, the titration regimen comprises administering a 1 mg siponimod dosage form, said administration leading in-vivo to a Cmax of 5 to 10 ng/ml, preferably 5.5 to 9.5 ng/ml, more preferably 6 to 9 ng/ml, still more preferably 7 to 8 ng/ml, and to a AUClast of 180 to 360 h·ng/ml, preferably 200 to 320 h·ng/ml, more preferably 220 to 300 h·ng/ml, still more preferably 240 to 280 h·ng/ml.

In a further preferred embodiment, the titration regimen comprises administering a 1 mg siponimod dosage form, the in-vivo AUC-time profile from time zero to infinity (AUCinf) of said dosage form being 190 to 370 h·ng/ml, preferably 220 to 340 h·ng/ml, more preferably 140 to 320 h·ng/ml, still more preferably 260 to 300 h·ng/ml.

In a further preferred embodiment of the invention, the titration regimen comprises administering a 1 mg siponimod dosage form, said administration leading in-vivo to a Tmax of 3 to 8 h, preferably 3 to 7 h, more preferably 3 to 6 h, most preferably 3 to 5 h.

In a further preferred embodiment, the titration regimen comprises administering a 2 mg siponimod dosage form, leading in-vivo to a Cmax of 10 to 20 ng/ml, preferably 14.0 to 17.0 ng/ml, more preferably 14.5 to 16.5 ng/ml, still more preferably 15.0 to 16.0 ng/ml, and to a AUClast of 300 to 700 h·ng/ml, preferably 500 to 560 h·ng/ml, more preferably 510 to 550 h·ng/ml, still more preferably 520 to 540 h·ng/ml.

In a further preferred embodiment, the titration regimen comprises administering a 2 mg siponimod dosage form, the in-vivo AUC-time profile from time zero to infinity (AUCinf) of said dosage form being 350 to 750 h·ng/ml, preferably 520 to 600 h·ng/ml, more preferably 540 to 580 h·ng/ml, still more preferably 550 to 570 h·ng/ml.

In a further preferred embodiment of the invention, the titration regimen comprises administering a 1 mg siponimod dosage form, said administration leading in-viva to a Tmax of 3 to 8 h, preferably 3 to 7 h, more preferably 3 to 6 h, most preferably 3 to 5 h.

Siponimod Maintenance Regimen and Titration Regimen

Generally, the term "maintenance regimen" as used herein refers to the administration of siponimod after the up-titration is completed. Said maintenance regime comprises the administration of the maintenance dose of 1-15 mg siponimod, preferably 1-10 mg siponimod, more preferably 1-5 mg siponimod, most preferably 1-2 mg siponimod. Preferably, the maintenance regime is carried out continuously, far example over several days, weeks, months or years.

In one embodiment, the initial titration regimen comprises administering siponimod such that the dosage administered on a specific day of the initial titration regimen is the sum of the dosages administered on the previous two days within a range of ±40%.

In general, the titration regimen is continued until the maintenance dose is reached. In one embodiment, the titration regimen is conducted over 3-10 days, whereafter the maintenance dose is administered. In a preferred embodiment, the titration regimen is conducted over 6 days, whereby the maintenance dose is administered from day 6 onwards.

In one preferred embodiment, the maintenance regimen comprises the administration of 1 mg siponimod. In another preferred embodiment, the maintenance regime comprises the administration of 2 mg siponimod.

In one embodiment, in the titration regimen dosage forms comprising 0.25 mg, 0.5 mg, 1 mg or 2 mg siponimod are used.

In one embodiment, in the titration regimen immediate release dosage forms comprising 0.25 mg, 0.5 mg, 1 mg or 2 mg siponimod are used.

In one embodiment of the invention, siponimod is administered once daily in the maintenance regimen as well as in the titration regimen.

In one embodiment, the titration regimen comprises one administration of a dosage form comprising 0.25 mg siponimod at day 1, one administration of a dosage form comprising 0.25 mg siponimod at day 2, one administration of a dosage form comprising 0.5 mg siponimod at day 3, one concomitant administration of a dosage form comprising 0.5 mg siponimod together with a dosage form comprising 0.25 mg siponimod at day 4, one concomitant administration of a dosage form comprising 1 mg siponimod together with a dosage form comprising 0.25 mg siponimod at day 5, and one administration of a dosage form comprising 2 mg siponimod at day 6.

Preferably, an immediate release dosage form is administered in the maintenance regimen as well as in the titration regimen.

In a preferred embodiment of the invention, an immediate release dosage form comprising 2 mg siponimod is administered once daily to a patient as a maintenance regimen, after the patient has experienced a titration regimen of 0.25 mg siponimod at day 1, 0.25 mg siponimod at day 2, 0.5 mg siponimod at day 3, 0.75 mg siponimod at day 4, 1.25 mg siponimod at day 5, and 2 mg siponimod at day 6.

In a preferred embodiment of the invention, the siponimod used in the titration regimen and in the maintenance regimen is siponimod hemifumarate. Generally, all explanations given above of preferred embodiments of siponimod (e.g. salts, particle size), excipients and dissolution behaviour preferably apply to the dosage form of the maintenance regimen as well as to the dosage form of the titration regimen.

Beta-Blockers

Beta-blockers are a well-known family of beta adrenergic receptor antagonists that function as competitive pharmacologic inhibitors of catecholamine actions. It is known in the field that beta-blockers have widespread utility in the treatment of cardiovascular and non-cardiovascular diseases, in particular hypertension, angina pectoris, tremor and migraine. In one embodiment of the invention, the beta-blocker propranolol is used in the treatment of hypertension. Typically, treatment with propranolol comprises administering a daily dose of 30 to 320 mg propranolol, e.g. 80 mg propranolol. Typical dosage forms comprise 10, 40 or 80 mg propranolol.

Beta-blockers include propranolol (Dociton™, Inderal™), atenolol (Tenormin™), carteolol (Cartrol™, Ocupress™), carvedilol (Coreg™, Kredex™), labetalol (Normodyne™, Trandate™), nadolol (Corgard™), oxprenolol (Trasacor™, Tevacor™), penbutolol (Levatol™, Betapressin™), pindolol (Visken™, Betapindol™), sotalol (Betapace™, Sotalex™), timolol (Betfmol™, Timoptic™), acebutolol (Sectral™, Prent™), betaxolol (Betoptic™, Lokren™), bisoprolol (Zebeta™), celiprolol (Cardem™, Selectol™), esmolol (Brevibloc™), metoprolol (Lopressor™, Toprol-XL™) and nebivolol (Nebiliet™, Bystolic™).

The structure/chemical name of an active ingredient identified by a generic or trade name may be taken from the current edition of a standard compendium, e.g. "The Merck Index", or from a database, e.g. Patents international (e.g. IMS World Publications). The corresponding contents thereof are herewith incorporated hereinto by reference. Any person skilled in the art is fully enabled to identify the active ingredients based on these references.

Preferably, the beta-blocker is selected from the group consisting of propranolol, atenolol, carteolol, carvedilol, labetalol, nadolol, oxprenolol, penbutolol, pindolol, sotalol, timolol, acebutolol, betaxolol, bisoprolol, celiprolol, esmolol, metoprolol and nebivolol.

In one embodiment, the beta-blocker as used in the context of the invention is propranolol.

In one embodiment, the beta-blocker as used in the context of the invention is atenolol.

In one embodiment, the beta-blocker as used in the context of the invention is carteolol.

In one embodiment, the beta-blocker as used in the context of the invention is carvedilol.

In one embodiment, the beta-blocker as used in the context of the invention is labetalol.

In one embodiment, the beta-blocker as used in the context of the invention is nadolol.

In one embodiment, the beta-blocker as used in the context of the invention is oxprenolol.

In one embodiment, the beta-blocker as used in the context of the invention is penbutolol.

In one embodiment, the beta-blocker as used in the context of the invention is pindolol.

In one embodiment, the beta-blocker as used in the context of the invention is sotalol.

In one embodiment, the beta-blocker as used in the context of the invention is timolol.

In one embodiment, the beta-blocker as used in the context of the invention is acebutolol.

In one embodiment, the beta-blocker as used in the context of the invention is betaxolol.

In one embodiment, the beta-blocker as used in the context of the invention is bisoprolol.

In one embodiment, the beta-blocker as used in the context of the invention is celiprolol.

In one embodiment, the beta-blocker as used in the context of the invention is esmolol.

In one embodiment, the beta-blocker as used in the context of the invention is metoprolol.

In one embodiment, the beta-blocker as used in the context of the invention is nebivolol.

It will be understood, that a reference to an active ingredient throughout the description and the claims includes said active ingredient in free form and in form of a pharmaceutically acceptable salt. If an active ingredient has, e.g., at least one basic center, it can form an acid addition salt. An active ingredient having at least one acidic group can form a salt with a base. An active ingredient, in free form or in pharmaceutically acceptable salt form, may be in the form of a hydrate and/or may include other solvents, for example solvents used for the crystallization of a compound in solid form.

A "pharmaceutically acceptable salt" is intended to mean a salt of a free base/free acid of an active ingredient that is not toxic, biologically intolerable, or otherwise biologically undesirable. Preferred pharmaceutically acceptable salts are those that are pharmacologically effective and suitable for contact with the tissues of patients without undue toxicity, irritation, or allergic response. Such salts are known in the field (e.g. S M Berge et al, "Pharmaceutical Salts", J Pharm Sd, 1977, 66:1-19; and "Handbook of Pharmaceutical Salts, Properties, Selection, and Use", R H Stahl, C G Wermuth, Eds, Wiley-VCH and VHCA: Zurich, 2002).

Clinically Relevant Scenario 1

In accordance with a first aspect of the invention, there is provided a method of treating an autoimmune disease in a patient comprising
  a) administering to said patient an initial titration regimen of siponimod;
  b) administering to said patient 1-15 mg siponimod daily as a maintenance regimen; and
  c) introducing in said patient a beta-blocker treatment the earliest at the first day when said patient is receiving the dosage of the maintenance regimen;
  wherein said initial titration regimen comprises administering siponimod at a dosage lower than the dosage of the maintenance regimen and then increasing the dosage stepwise up to the dosage of the maintenance regimen.

In a preferred embodiment of the first aspect of the invention, there is provided a method of treating secondary progressive multiple sclerosis in a patient comprising
  a) administering to said patient an initial titration regimen of siponimod;
  b) administering to said patient an immediate release dosage form comprising 2 mg siponimod once daily as a maintenance regimen; and
  c) introducing in said patient a beta-blocker treatment the earliest at the first day when said patient is receiving the dosage of the maintenance regimen;
  wherein said initial titration regimen comprises one administration of 0.25 mg siponimod at day 1, one administration of 0.25 mg siponimod at day 2, one administration of 0.5 mg siponimod at day 3, one administration of 0.75 mg siponimod at day 4, one administration of 1.25 mg siponimod at day 5, and one administration of 2 mg siponimod at day 6; and
  wherein, in said initial titration regimen, immediate release dosage forms comprising 0.25 mg, 0.5 mg, 1 mg and 2 mg siponimod are used.

In a further preferred embodiment of the first aspect of the invention, there is provided a method of treating secondary progressive multiple sclerosis in a patient comprising
  a) administering to said patient an initial titration regimen of siponimod;

b) administering to said patient an immediate release dosage form comprising 2 mg siponimod once daily as a maintenance regimen; and c) introducing in said patient a beta-blocker treatment the earliest at the first day when a pharmacokinetic steady state of siponimod is reached;

wherein said initial titration regimen comprises one administration of 0.25 mg siponimod at day 1, one administration of 0.25 mg siponimod at day 2, one administration of 0.5 mg siponimod at day 3, one administration of 0.75 mg siponimod at day 4, one administration of 1.25 mg siponimod at day 5, and one administration of 2 mg siponimod at day 6; and wherein, in said initial titration regimen, immediate release dosage forms comprising 0.25 mg, 0.5 mg, 1 mg and 2 mg siponimod are used.

Clinically Relevant Scenario 2

In accordance with a second aspect of the invention, there is provided a method of treating an autoimmune disease in a patient receiving a chronic beta-blocker treatment and having a resting heart rate of >50 bpm under said chronic beta-blocker treatment comprising introducing in said patient a siponimod treatment by a) administering to said patient an initial titration regimen of siponimod; and b) administering to said patient 1-15 mg siponimod daily as a maintenance regimen;

wherein said initial titration regimen comprises administering siponimod at a dosage lower than the dosage of the maintenance regimen and then increasing the dosage stepwise up to the dosage of the maintenance regimen.

In a preferred embodiment of the second aspect of the invention, there is provided a method of treating secondary progressive multiple sclerosis in a patient receiving a chronic beta-blocker treatment and having a resting heart rate of >50 bpm under said chronic beta-blocker treatment comprising introducing in said patient a siponimod treatment by a) administering to said patient an initial titration regimen of siponimod; and b) administering to said patient an immediate release dosage form comprising 2 mg siponimod once daily as a maintenance regimen;

wherein said initial titration regimen consists of one administration of 0.25 mg siponimod at day 1, one administration of 0.25 mg siponimod at day 2, one administration of 0.5 mg siponimod at day 3, one administration of 0.75 mg siponimod at day 4, one administration of 1.25 mg siponimod at day 5 and one administration of 2 mg siponimod at day 6; and wherein, in said initial titration regimen, immediate release dosage forms comprising 0.25 mg, 0.5 mg, 1 mg and 2 mg siponimod are used.

In a third aspect of the invention, there is provided a method of treating an autoimmune disease in a patient receiving a chronic beta-blocker treatment and having a resting heart rate of ≤50 bpm under said chronic beta-blocker treatment comprising a) interrupting said chronic beta-blocker treatment in said patient until the baseline heart-rate is >50 bpm;

b) initiating in said patient a siponimod treatment by
b1) administering to said patient an initial titration regimen of siponimod; and
b2) administering to said patient 1-15 mg siponimod daily as a maintenance regimen; and c) re-initiating in said patient a beta-blocker treatment the earliest at the first day when said patient is receiving the dosage of the maintenance regimen;

wherein said initial titration regimen comprises administering siponimod at a dosage lower than the dosage of the maintenance regimen and then increasing the dosage stepwise up to the dosage of the maintenance regimen.

In a preferred embodiment of the third aspect of the invention, there is provided a method of treating secondary progressive multiple sclerosis in a patient receiving a chronic beta-blocker treatment and having a resting heart rate of ≤50 bpm under said chronic beta-blocker treatment comprising a) interrupting said chronic beta-blocker treatment in said patient until the baseline heart-rate is >50 bpm;

b) initiating in said patient a siponimod treatment by
b1) administering to said patient an initial titration regimen of siponimod; and
b2) administering to said patient an immediate release dosage form comprising 2 mg siponimod once daily as a maintenance regimen; and c) re-initiating in said patient a beta-blocker treatment after 2 weeks of treatment with siponimod;

wherein said initial titration regimen consists of one administration of 0.25 mg siponimod at day 1, one administration of 0.25 mg siponimod at day 2, one administration of 0.5 mg siponimod at day 3, one administration of 0.75 mg siponimod at day 4, one administration of 1.25 mg siponimod at day 5 and one administration of 2 mg siponimod at day 6; and wherein, in said titration regimen, immediate release dosage forms comprising 0.25 mg, 0.5 mg, 1 mg and 2 mg siponimod are used.

Further Definitions and Embodiments of the Invention

The terms "treatment"/"treating" as used herein includes: (1) preventing or delaying the appearance of clinical symptoms of the state, disorder or condition developing in an animal, particularly a mammal and especially a human, that may be afflicted with or predisposed to the state, disorder or condition but does not yet experience or display clinical or subclinical symptoms of the state, disorder or condition; (2) inhibiting the state, disorder or condition (e.g. arresting, reducing or delaying the development of the disease, or a relapse thereof in case of maintenance treatment, of at least one clinical or subclinical symptom thereof); and/or (3) relieving the condition (i.e. causing regression of the state, disorder or condition or at least one of its clinical or subclinical symptoms). The benefit to a patient to be treated is either statistically significant or at least perceptible to the patient or to the physician. However, it will be appreciated that when a medicament is administered to a patient to treat a disease, the outcome may not always be effective treatment.

In one embodiment, the siponimod as used in the context of the present invention is effective to reduce a symptom of relapsing remitting multiple sclerosis (RRMS) or secondary progressive multiple sclerosis (SPMS), preferably SPMS. In one embodiment, the symptom is an MRI-monitored multiple sclerosis disease activity, disability progression, brain atrophy, neuronal dysfunction, neuronal injury, neuronal degeneration, deterioration of visual function, impaired mobility, cognitive impairment, reduction of brain volume, deterioration in general health status, functional status and/or quality of life.

In another embodiment, the siponimod as used in the context of the present invention is effective to reduce a symptom of polymyositis or dermatomyositis, preferably polymyositis. In one embodiment, the symptom is pain, with marked weakness and/or loss of muscle mass in the muscles of the head, neck, torso and upper arms and legs. In one embodiment, the symptom is dysphagia, low grad fever, peripheral adenopathy, foot drop and interstitial lung disease.

An example of an autoimmune condition according to the present invention is multiple sclerosis (MS), for example relapsing-remitting MS (RRMS), primary progressive MS (PPMS), secondary progressive MS (SPMS) and relapsing SPMS. Preferably, the siponimod as used in the context of the present invention is used for treating RRMS and/or SPMS, most preferably SPMS.

A further example of an autoimmune condition according to the present invention is inflammatory myopathy, for example polymyositis and dermatomyositis. Preferably, the siponimod as used in the context of the present invention is used for treating polymyositis.

The expression "introducing a beta-blocker treatment" as used herein means administering a first dose of beta-blocker according to the respective summary of product characteristics (SmPC). In the context of the present invention, beta-blocker treatment is introduced the earliest at the first day of administration of the dosage of the siponimod maintenance regimen, preferably when a pharmacokinetic steady state of siponimod is reached. A pharmacokinetic steady state of siponimod is reached in general during the maintenance regimen, however the exact point in time may vary between patients, e.g. depending on their disease/disease state.

The expression "introducing a siponimod treatment" as used herein means administering an initial titration regimen of siponimod, followed by administering a respective maintenance regimen.

The expression "re-initiating a beta-blocker treatment" as used herein means administering a first dose of beta-blocker according to the respective summary of product characteristics (SmPC), following a beta-blocker treatment holiday, which in some cases might be necessary due to upcoming introduction of siponimod treatment. In a preferred embodiment of the invention, beta-blocker treatment is re-initiated 8 days after the siponimod titration regimen has been concluded. In a particularly preferred embodiment, the siponimod titration regimen is distributed over 6 days and beta-blocker treatment is re-initiated after 2 weeks of treatment with siponimod, i.e. 2 weeks after the first administration of siponimod.

It is common knowledge in the field that discontinuation of beta-blocker therapy may be accompanied by withdrawal syndromes, such as hyperadrenergic symptoms, exacerbations of angina, acute myocardial infarction and sudden death. Generally, beta-blockers should be tapered slowly rather than discontinued abruptly. Accordingly, the expression "interruption of beta-blocker treatment" as used herein means interruption according to the SmPC of the beta-blocker in question.

The term "resting heart rate" (RHR) as used herein means the number of contractions of the heart that occur in a single minute while the body is at complete rest. This number will vary depending upon the age, gender, and general health of a person.

As used herein, "bradycardia" typically refers to a RHR<50 bpm.

The term "baseline heart rate" as used herein means a referential heart rate to which other heart rates, such as the heart rate under chronic beta-blocker treatment, can be compared to. Typically, the RHR in the absence of any heart rate-affecting medication serves as the baseline heart rate.

The abbreviation "HR" as used herein means "heart rate". A person having ordinary skill in the art will typically measure the HR using an electrocardiograph.

The expression "$E_{max}$" as used herein means the maximum change from baseline in time matched, hourly average HR.

The expression "$FEV_1$" as used herein is a pulmonary parameter and means "forced expiratory volume in 1 second". A person having ordinary skill in the art will be well acquainted with the assessment of $FEV_1$ and will follow the standard pulmonary laboratory practice, which is consistent with the American Thoracic Society/European Respiratory Society Standardization of Spirometry.

The abbreviation "AVB" as used herein means "atrioventricular block".

The abbreviation "SP" as used herein means "sinus pause", also known as sinoatrial arrest.

A further aspect of the invention comprises the following enumerated embodiments:

Enumerated Embodiment 1: A method of treating an autoimmune disease in a patient comprising
  a) administering to said patient an initial titration regimen of siponimod;
  b) administering to said patient 1-15 mg siponimod daily as a maintenance regimen; and
  c) introducing in said patient a beta-blocker treatment the earliest at the first day when said patient is receiving the dosage of the maintenance regimen;
wherein said initial titration regimen comprises administering siponimod at a dosage lower than the dosage of the maintenance regimen and then increasing the dosage stepwise up to the dosage of the maintenance regimen.

Enumerated Embodiment 2: The method according to enumerated embodiment 1, wherein said autoimmune disease is selected from inflammatory myopathy and multiple sclerosis.

Enumerated Embodiment 3: The method according to enumerated embodiment 1, wherein said autoimmune disease is selected from polymyositis, dermatomyositis, inclusion-body myositis and secondary progressive multiple sclerosis.

Enumerated Embodiment 4: The method according to enumerated embodiment 1, wherein said autoimmune disease is secondary progressive multiple sclerosis.

Enumerated Embodiment 5: The method according to any one of the preceding enumerated embodiments, wherein the maintenance regimen administered in step b) of said method comprises 2-10 mg siponimod.

Enumerated Embodiment 6: The method according to enumerated embodiment 5, wherein said maintenance regimen comprises 2-5 mg siponimod.

Enumerated Embodiment 7: The method according to any one of the preceding enumerated embodiments, wherein the maintenance regimen administered in step b) of said method is administered once daily.

Enumerated Embodiment 8: The method according to any one of the preceding enumerated embodiments, wherein in the maintenance regimen administered in step b) of said method an immediate release dosage form is used.

Enumerated Embodiment 9: The method according to any one of the preceding enumerated embodiments, wherein said initial titration regimen comprises administering siponimod such that the dosage administered on a specific day of the initial titration regimen is the sum of the dosages administered on the previous two days within a range of ±40%.

Enumerated Embodiment 10: The method according to any one of the preceding enumerated embodiments, wherein said initial titration regimen is conducted over 3-10 days.

Enumerated Embodiment 11: The method according to any one of the preceding enumerated embodiments, wherein the dosage of the maintenance regimen is 2 mg siponimod and wherein said initial titration regimen comprises administering 0.25 mg siponimod at day 1, 0.25 mg of siponimod at day 2, 0.5 mg siponimod at day 3, 0.75 mg siponimod at day 4, 1.25 mg siponimod at day 5 and 2 mg siponimod at day 6.

Enumerated Embodiment 12: The method according to enumerated embodiment 11, wherein said initial titration regimen comprises one administration of 0.25 mg siponimod at day 1, one administration of 0.25 mg siponimod at day 2, one administration of 0.5 mg siponimod at day 3, one administration of 0.75 mg siponimod at day 4, one administration of 1.25 mg siponimod at day 5 and one administration of 2 mg siponimod at day 6.

Enumerated Embodiment 13: The method according to enumerated embodiment 12, wherein, in said initial titration regimen, immediate release dosage forms comprising 0.25 mg, 0.5 mg, 1 mg and 2 mg siponimod are used.

Enumerated Embodiment 14: The method according to enumerated embodiment 1, wherein
said autoimmune disease is secondary progressive multiple sclerosis;
wherein the maintenance regimen administered in step b) of said method is an immediate release dosage form comprising 2 mg siponimod;
wherein the maintenance regimen administered in step b) of said method is administered once daily;
wherein the initial titration regimen administered in step a) of said method comprises one administration of 0.25 mg siponimod at day 1, one administration of 0.25 mg siponimod at day 2, one administration of 0.5 mg siponimod at day 3, one administration of 0.75 mg siponimod at day 4, one administration of 1.25 mg siponimod at day 5 and one administration of 2 mg siponimod at day 6; and
wherein in the initial titration regimen administered in step a) of said method immediate release dosage forms comprising 0.25 mg, 0.5 mg, 1 mg and 2 mg siponimod are used.

Enumerated Embodiment 15: A method of treating secondary progressive multiple sclerosis in a patient comprising
a) administering to said patient an initial titration regimen of siponimod;
b) administering to said patient an immediate release dosage form comprising 2 mg siponimod once daily as a maintenance regimen; and
c) introducing in said patient a beta-blocker treatment the earliest at the first day when said patient is receiving the dosage of the maintenance regimen;
wherein said initial titration regimen comprises one administration of 0.25 mg siponimod at day 1, one administration of 0.25 mg siponimod at day 2, one administration of 0.5 mg siponimod at day 3, one administration of 0.75 mg siponimod at day 4, one administration of 1.25 mg siponimod at day 5 and one administration of 2 mg siponimod at day 6; and
wherein, in said initial titration regimen, immediate release dosage forms comprising 0.25 mg, 0.5 mg, 1 mg and 2 mg siponimod are used.

Enumerated Embodiment 16: Siponimod for use in the treatment of an autoimmune disease in a patient comprising
a) administering to said patient an initial titration regimen of siponimod;
b) administering to said patient 1-15 mg siponimod daily as a maintenance regimen; and
c) introducing in said patient a beta-blocker treatment the earliest at the first day when said patient is receiving the dosage of the maintenance regimen;
wherein said initial titration regimen comprises administering siponimod at a dosage lower than the dosage used as a maintenance regimen and then increasing the dosage stepwise up to the dosage of the maintenance regimen.

Enumerated Embodiment 17: Siponimod for use in the treatment of secondary progressive multiple sclerosis in a patient comprising
a) administering to said patient an initial titration regimen of siponimod;
b) administering to said patient an immediate release dosage form comprising 2 mg siponimod once daily as a maintenance regimen; and
c) introducing in said patient a beta-blocker treatment the earliest at the first day when said patient is receiving the dosage of the maintenance regimen;
wherein said initial titration regimen comprises one administration of 0.25 mg siponimod at day 1, one administration of 0.25 mg siponimod at day 2, one administration of 0.5 mg siponimod at day 3, one administration of 0.75 mg siponimod at day 4, one administration of 1.25 mg siponimod at day 5 and one administration of 2 mg siponimod at day 6; and
wherein, in said initial titration regimen, immediate release dosage forms comprising 0.25 mg, 0.5 mg, 1 mg and 2 mg siponimod are used.

Enumerated Embodiment 18: Use of siponimod in the manufacture of a medication for the treatment of an autoimmune disease in a patient comprising
a) administering to said patient an initial titration regimen of siponimod;
b) administering to said patient 1-15 mg siponimod daily as a maintenance regimen; and
c) introducing in said patient a beta-blocker treatment the earliest at the first day when said patient is receiving the dosage of the maintenance regimen;
wherein said initial titration regimen comprises administering siponimod at a dosage lower than the dosage used as a maintenance regimen and then increasing the dosage stepwise up to the dosage of the maintenance regimen.

Enumerated Embodiment 19: Use of siponimod in the manufacture of a medication for the treatment of secondary progressive multiple sclerosis in a patient comprising
a) administering to said patient an initial titration regimen of siponimod;
b) administering to said patient an immediate release dosage form comprising 2 mg siponimod once daily as a maintenance regimen; and
c) introducing in said patient a beta-blocker treatment the earliest at the first day when said patient is receiving the dosage of the maintenance regimen;

wherein said initial titration regimen comprises one administration of 0.25 mg siponimod at day 1, one administration of 0.25 mg siponimod at day 2, one administration of 0.5 mg siponimod at day 3, one administration of 0.75 mg siponimod at day 4, one administration of 1.25 mg siponimod at day 5 and one administration of 2 mg siponimod at day 6; and wherein, in said initial titration regimen, immediate release dosage forms comprising 0.25 mg, 0.5 mg, 1 mg and 2 mg siponimod are used.

Enumerated Embodiment 20: A method of treating an autoimmune disease in a patient receiving a chronic beta-blocker treatment and having a resting heart rate of >50 bpm under said chronic beta-blocker treatment comprising introducing in said patient a siponimod treatment by
  a) administering to said patient an initial titration regimen of siponimod; and
  b) administering to said patient 1-15 mg siponimod daily as a maintenance regimen;
wherein said initial titration regimen comprises administering siponimod at a dosage lower than the dosage used as a maintenance regimen and then increasing the dosage stepwise up to the dosage of the maintenance regimen.

Enumerated Embodiment 21: The method according to enumerated embodiment 20, wherein said autoimmune disease is selected from inflammatory myopathy and multiple sclerosis.

Enumerated Embodiment 22: The method according to enumerated embodiment 20, wherein said autoimmune disease is selected from polymyositis, dermatomyositis, inclusion-body myositis and secondary progressive multiple sclerosis.

Enumerated Embodiment 23: The method according to enumerated embodiment 20, wherein said autoimmune disease is secondary progressive multiple sclerosis.

Enumerated Embodiment 24: The method according to any one of enumerated embodiments 20 to 23, wherein the maintenance regimen administered in step b) of said method comprises 2-10 mg siponimod.

Enumerated Embodiment 25: The method according to enumerated embodiment 24, wherein said maintenance regimen comprises 2-5 mg siponimod.

Enumerated Embodiment 26: The method according to any one of enumerated embodiments 20 to 25, wherein the maintenance regimen administered in step b) of said method is administered once daily.

Enumerated Embodiment 27: The method according to any one of enumerated embodiments 20 to 26, wherein the maintenance regimen administered in step b) of said method is administered as an immediate release dosage form.

Enumerated Embodiment 28: The method according to any one of enumerated embodiments 20 to 27, wherein said initial titration regimen comprises administering siponimod such that the dosage administered on a specific day of the initial titration regimen is the sum of the dosages administered on the previous two days within a range of ±40%.

Enumerated Embodiment 29: The method according to any one of enumerated embodiments 20 to 28, wherein said initial titration regimen is conducted over 3-10 days.

Enumerated Embodiment 30: The method according to any one of enumerated embodiments 20 to 29, wherein the dosage of the maintenance regimen is 2 mg siponimod and wherein said initial titration regimen comprises administering 0.25 mg siponimod at day 1, 0.25 mg of siponimod at day 2, 0.5 mg siponimod at day 3, 0.75 mg siponimod at day 4, 1.25 mg siponimod at day 5, and 2 mg siponimod at day 6.

Enumerated Embodiment 31: The method according to enumerated embodiment 30, wherein said initial titration regimen comprises one administration of 0.25 mg siponimod at clay 1, one administration of 0.25 mg siponimod at day 2, one administration of 0.5 mg siponimod at day 3, one administration of 0.75 mg siponimod at day 4, one administration of 1.25 mg siponimod at day 5 and one administration of 2 mg siponimod at day 6.

Enumerated Embodiment 32: The method according to enumerated embodiment 31, wherein, in said initial titration regimen, immediate release dosage forms comprising 0.25 mg, 0.5 mg, 1 mg and 2 mg siponimod are used.

Enumerated Embodiment 33: The method according to enumerated embodiment 20, wherein said autoimmune disease is secondary progressive multiple sclerosis;
  wherein the maintenance regimen administered in step b) of said method is an immediate release dosage form comprising 2 mg siponimod;
  wherein the maintenance regimen administered in step b) of said method is administered once daily;
  wherein the initial titration regimen administered in step a) of said method comprises one administration of 0.25 mg siponimod at day 1, one administration of 0.25 mg siponimod at day 2, one administration of 0.5 mg siponimod at day 3, one administration of 0.75 mg siponimod at day 4, one administration of 1.25 mg siponimod at day 5 and one administration of 2 mg siponimod at day 6; and
  wherein in the initial titration regimen administered in step a) of said method immediate release dosage forms comprising 0.25 mg, 0.5 mg, 1 mg and 2 mg siponimod are used.

Enumerated Embodiment 34: A method of treating secondary progressive multiple sclerosis in a patient receiving a chronic beta-blocker treatment and having a resting heart rate of >50 bpm under said chronic beta-blocker treatment comprising introducing in said patient a siponimod treatment by
  a) administering to said patient an initial titration regimen of siponimod; and
  b) administering to said patient an immediate release dosage form comprising 2 mg siponimod once daily as a maintenance regimen;
wherein said initial titration regimen consists of one administration of 0.25 mg siponimod at day 1, one administration of 0.25 mg siponimod at day 2, one administration of 0.5 mg siponimod at day 3, one administration of 0.75 mg siponimod at day 4, one administration of 1.25 mg siponimod at day 5 and one administration of 2 mg siponimod at day 6; and wherein, in said initial titration regimen, immediate release dosage forms comprising 0.25 mg, 0.5 mg, 1 mg and 2 mg siponimod are used.

Enumerated Embodiment 35: Siponimod for use in the treatment of an autoimmune disease in a patient receiving a chronic beta-blocker treatment and having a resting heart rate of >59 bpm under said chronic beta-blocker treatment comprising introducing in said patient a siponimod treatment by
  a) administering to said patient an initial titration regimen of siponimod; and b) administering to said patient 1-15 mg siponimod daily as a maintenance regimen;

wherein said initial titration regimen comprises administering siponimod at a dosage lower than the dosage used as a maintenance regimen and then increasing the dosage stepwise up to the dosage of the maintenance regimen.

Enumerated Embodiment 36: Siponimod for use in the treatment of secondary progressive multiple sclerosis in a patient receiving a chronic beta-blocker treatment and having a resting heart rate of >50 bpm under said chronic beta-blocker treatment comprising introducing in said patient a siponimod treatment by
  a) administering to said patient an initial titration regimen of siponimod; and
  b) administering to said patient an immediate release dosage form comprising 2 mg siponimod once daily as a maintenance regimen;

wherein said initial titration regimen consists of one administration of 0.25 mg siponimod at day 1, one administration of 0.25 mg siponimod at day 2, one administration of 0.5 mg siponimod at day 3, one administration of 0.75 mg siponimod at day 4, one administration of 1.25 mg siponimod at day 5 and one administration of 2 mg siponimod at day 6; and wherein, in said initial titration regimen, immediate release dosage forms comprising 0.25 mg, 0.5 mg, 1 mg and 2 mg siponimod are used.

Enumerated Embodiment 37: Use of siponimod for the manufacture of a medication for the treatment of an autoimmune disease in a patient receiving a chronic beta-blocker treatment and having a resting heart rate of >50 bpm under said chronic beta-blocker treatment comprising introducing in said patient a siponimod treatment by
  a) administering to said patient an initial titration regimen of siponimod; and
  b) administering to said patient 1-15 mg siponimod daily as a maintenance regimen;

wherein said initial titration regimen comprises administering siponimod at a dosage lower than the dosage used as a maintenance regimen and then increasing the dosage stepwise up to the dosage of the maintenance regimen.

Enumerated Embodiment 38: Use of siponimod for the manufacture of a medication for the treatment of secondary progressive multiple sclerosis in a patient receiving a chronic beta-blocker treatment and having a resting heart rate of >50 bpm under said chronic beta-blocker treatment comprising introducing in said patient a siponimod treatment by
  a) administering to said patient an initial titration regimen of siponimod; and
  b) administering to said patient an immediate release dosage form comprising 2 mg siponimod once daily as a maintenance regimen;

wherein said initial titration regimen consists of one administration of 0.25 mg siponimod at day 1, one administration of 0.25 mg siponimod at day 2, one administration of 0.5 mg siponimod at day 3, one administration of 0.75 mg siponimod at day 4, one administration of 1.25 mg siponimod at day 5 and one administration of 2 mg siponimod at day 6; and wherein, in said initial titration regimen, immediate release dosage forms comprising 0.25 mg, 0.5 mg, 1 mg and 2 mg siponimod are used.

Enumerated Embodiment 39: A method of treating an autoimmune disease in a patient receiving a chronic beta-blocker treatment and having a resting heart rate of ≤50 bpm under said chronic beta-blocker treatment comprising
  a) interrupting said chronic beta-blocker treatment in said patient until the baseline heart-rate is >50 bpm;
  b) administering to said patient an initial titration regimen of siponimod; and initiating in said patient a siponimod treatment by
    b1) administering to said patient an initial titration regimen of siponimod; and
    b2) administering to said patient 1-15 mg siponimod daily as a maintenance regimen; and
  c) re-initiating in said patient a beta-blocker treatment the earliest at the first day when said patient is receiving the dosage of the maintenance regimen;

wherein said initial titration regimen comprises administering siponimod at a dosage lower than the dosage used as a maintenance regimen and then increasing the dosage stepwise up to the dosage of the maintenance regimen.

Enumerated Embodiment 40: The method according to enumerated embodiment 39, wherein said autoimmune disease is selected from inflammatory myopathy and multiple sclerosis.

Enumerated Embodiment 41: The method according to enumerated embodiment 39, wherein said autoimmune disease is selected from polymyositis, dermatomyositis, inclusion-body myositis and secondary progressive multiple sclerosis.

Enumerated Embodiment 42: The method according to enumerated embodiment 39, wherein said autoimmune disease is secondary progressive multiple sclerosis.

Enumerated Embodiment 43: The method according to any one of enumerated embodiments 39 to 42, wherein the maintenance regimen administered in step b2) of said method comprises 2-10 mg siponimod.

Enumerated Embodiment 44: The method according to enumerated embodiment 43, wherein said maintenance regimen comprises 2-5 mg siponimod.

Enumerated Embodiment 45: The method according to any one of enumerated embodiments 39 to 44, wherein the maintenance regimen administered in step b2) of said method is administered once daily.

Enumerated Embodiment 46: The method according to any one of enumerated embodiments 39 to 45, wherein the maintenance regimen administered in step b2) of said method is administered as an immediate release dosage form.

Enumerated Embodiment 47: The method according to any one of enumerated embodiments 39 to 46, wherein said initial titration regimen comprises administering siponimod such that the dosage administered on a specific day of the initial titration regimen is the sum of the dosages administered on the previous two days within a range of ±40%.

Enumerated Embodiment 48: The method according to any one of enumerated embodiments 39 to 47, wherein said initial titration regimen is conducted over 3-10 days.

Enumerated Embodiment 49: The method according to any one of enumerated embodiments 39 to 48, wherein the dosage of the maintenance regimen is 2 mg siponimod and wherein said initial titration regimen comprises administering 0.25 mg siponimod at day 1, 0.25 mg of siponimod at day 2, 0.5 mg siponimod at day 3, 0.75 mg siponimod at day 4, 1.25 mg siponimod at day 5 and 2 mg siponimod at day 6.

Enumerated Embodiment 50: The method according to enumerated embodiment 49, wherein said initial titration regimen comprises one administration of 0.25 mg siponimod at day 1, one administration of 0.25 mg siponimod at day 2, one administration of 0.5 mg siponimod at day 3, one administration of 0.75 mg siponimod at day 4, one administration of 1.25 mg siponimod at day 5 and one administration of 2 mg siponimod at day 6.

Enumerated Embodiment 51: The method according to enumerated embodiment 50, wherein, in said initial titration regimen, immediate release dosage forms comprising 0.25 mg, 0.5 mg, 1 mg and 2 mg siponimod are used.

Enumerated Embodiment 52: The method according to any one of enumerated embodiments 39 to 51, wherein the beta-blocker treatment re-initiated in step c) of said method is re-initiated after 2-3 weeks of treatment with siponimod.

Enumerated Embodiment 53: The method according to enumerated embodiment 39 wherein said autoimmune disease is secondary progressive multiple sclerosis;
wherein the maintenance regimen administered in step b2) of said method is an immediate release dosage form comprising 2 mg siponimod;
wherein the maintenance regimen administered in step b2) of said method is administered once daily;
wherein the initial titration regimen administered in step b1) of said method comprises one administration 010.25 mg siponimod at day 1, one administration of 0.25 mg siponimod at day 2, one administration of 0.5 mg siponimod at day 3, one administration of 0.75 mg siponimod at day 4, one administration of 1.25 mg siponimod at day 5 and one administration of 2 mg siponimod at day 6;
in the initial titration regimen administered in step b1) of said method immediate release dosage forms comprising 0.25 mg, 0.5 mg, 1 mg and 2 mg siponimod are used; and
wherein the beta-blocker treatment re-initiated in step c) of said method is re-initiated after 2 weeks of treatment with siponimod.

Enumerated Embodiment 54: A method of treating secondary progressive multiple sclerosis in a patient receiving a chronic beta-blocker treatment and having a resting heart rate of bpm under said chronic beta-blocker treatment comprising
 a) interrupting said chronic beta-blocker treatment in said patient until the baseline heart-rate is >50 bpm;
 b) initiating in said patient a siponimod treatment by
  b1) administering to said patient an initial titration regimen of siponimod; and
  b2) administering to said patient an immediate release dosage form comprising 2 mg siponimod once daily as a maintenance regimen; and
 c) re-initiating in said patient a beta-blocker treatment after 2 weeks of treatment with siponimod;
wherein said initial titration regimen consists of one administration of 0.25 mg siponimod at day 1, one administration of 0.25 mg siponimod at day 2, one administration of 0.5 mg siponimod at day 3, one administration of 0.75 mg siponimod at day 4 one administration of 1.25 mg siponimod at day 5, and one administration of 2 mg siponimod at day 6; and wherein, in said titration regimen, immediate release dosage forms comprising 0.25 mg, 05 mg, 1 mg and 2 mg siponimod are used.

Enumerated Embodiment 55: Siponimod for use in the treatment of an autoimmune disease in a patient receiving a chronic beta-blocker treatment and having a resting heart rate of ≤50 bpm under said chronic beta-blocker treatment comprising
 a) interrupting said chronic beta-blocker treatment in said patient until the baseline heart-rate is >50 bpm;
 b) administering to said patient an initial titration regimen of siponimod; and initiating in said patient a siponimod treatment by
  b1) administering to said patient an initial titration regimen of siponimod; and
  b2) administering to said patient 1-15 mg siponimod daily as a maintenance regimen; and
 c) re-initiating in said patient a beta-blocker the earliest at the first day when said patient is receiving the dosage of the maintenance regimen;
wherein said initial titration regimen comprises administering siponimod at a dosage lower than the dosage used as a maintenance regimen and then increasing the dosage stepwise up to the dosage of the maintenance regimen.

Enumerated Embodiment 56: Siponimod for use in the treatment of secondary progressive multiple sclerosis in a patient receiving a chronic beta-blocker treatment and having a resting heart rate of ≤550 bpm under said chronic beta-blocker treatment comprising
 a) interrupting said chronic beta-blocker treatment in said patient until the baseline heart-rate is >50 bpm;
 b) initiating in said patient a siponimod treatment by
  b1) administering to said patient an initial titration regimen of siponimod; and
  b2) administering to said patient an immediate release dosage form comprising 2 mg siponimod once daily as a maintenance regimen; and
 c) re-initiating in said patient a beta-blocker treatment after 2 weeks of treatment with siponimod;
wherein said initial titration regimen consists of one administration of 0.25 mg siponimod at day 1, one administration of 0.25 mg siponimod at day 2, one administration of 0.5 mg siponimod at day 3, one administration of 0.75 mg siponimod at day 4, one administration of 1.25 mg siponimod at day 5 and one administration of 2 mg siponimod at day 6; and wherein, in said titration regimen, immediate release dosage forms comprising 0.25 mg, 0.5 mg, 1 mg and 2 mg siponimod are used.

Enumerated Embodiment 57: Use of siponimod for the manufacture of a medication for the treatment of an autoimmune disease in a patient receiving a chronic beta-blacker treatment and having a resting heart rate of ≤50 bpm under said chronic beta-blocker treatment comprising
 a) interrupting said chronic beta-blocker treatment in said patient until the baseline heart-rate is >50 bpm;
 b) administering to said patient an initial titration regimen of siponimod; and initiating in said patient a siponimod treatment by
  b1) administering to said patient an initial titration regimen of siponimod; and
  b2) administering to said patient 1-15 mg siponimod daily as a maintenance regimen; and
 c) re-initiating in said patient a beta-blocker treatment the earliest at the first day when said patient is receiving the dosage of the maintenance regimen;
wherein said initial titration regimen comprises administering siponimod at a dosage lower than the dosage used as a maintenance regimen and then increasing the dosage stepwise up to the dosage of the maintenance regimen.

Enumerated Embodiment 58: Use of siponimod for the manufacture of a medication for the treatment of secondary progressive multiple sclerosis in a patient receiving a chronic beta-blocker treatment and having a resting heart rate of 550 bpm under said chronic beta-blocker treatment comprising
a) interrupting said chronic beta-blocker treatment in said patient until the baseline heart-rate is >50 bpm;
b) initiating in said patient a siponimod treatment by
b1) administering to said patient an initial titration regimen of siponimod; and
b2) administering to said patient an immediate release dosage form comprising 2 mg siponimod once daily as a maintenance regimen; and
c) re-initiating in said patient a beta-blocker treatment after 2 weeks of treatment with siponimod;
wherein said initial titration regimen consists of one administration of 0.25 mg siponimod at day 1, one administration of 0.25 mg siponimod at day 2, one administration of 0.5 mg siponimod at day 3, one administration of 0.75 mg siponimod at day 4, one administration of 1.25 mg siponimod at day 5 and one administration of 2 mg siponimod at day 6; and wherein, in said titration regimen, immediate release dosage forms comprising 0.25 mg, 0.5 mg, 1 mg and 2 mg siponimod are used.

Enumerated Embodiment 59: A method of treating an autoimmune disease in a patient in need of a beta-blocker treatment comprising
a) administering to said patient an initial titration regimen of siponimod;
b) administering to said patient 1-15 mg siponimod daily as a maintenance regimen; and
c) introducing in said patient a beta-blocker treatment the earliest at the first day when said patient is receiving the dosage of the maintenance regimen;
wherein said initial titration regimen comprises administering siponimod at a dosage lower than the dosage of the maintenance regimen and then increasing the dosage stepwise up to the dosage of the maintenance regimen.

Enumerated Embodiment 60: A method of treating an autoimmune disease in a patient in need of a beta-blocker treatment, receiving a chronic beta-blocker treatment and having a resting heart rate of >50 bpm under said chronic beta-blocker treatment comprising introducing in said patient a siponimod treatment by
a) administering to said patient an initial titration regimen of siponimod; and
b) administering to said patient 1-15 mg siponimod daily as a maintenance regimen;
wherein said initial titration regimen comprises administering siponimod at a dosage lower than the dosage used as a maintenance regimen and then increasing the dosage stepwise up to the dosage of the maintenance regimen.

Enumerated Embodiment 61: A method of treating an autoimmune disease in a patient in need of a beta-blocker treatment, receiving a chronic beta-blocker treatment and having a resting heart rate of ≤50 bpm under said chronic beta-blocker treatment comprising
a) interrupting said chronic beta-blocker treatment in said patient until the baseline heart-rate is >50 bpm;
b) administering to said patient an initial titration regimen of siponimod; and initiating in said patient a siponimod treatment by
b1) administering to said patient an initial titration regimen of siponimod; and
b2) administering to said patient 1-15 mg siponimod daily as a maintenance regimen; and
c) re-initiating in said patient a beta-blocker treatment the earliest at the first day when said patient is receiving the dosage of the maintenance regimen;
wherein said initial titration regimen comprises administering siponimod at a dosage lower than the dosage used as a maintenance regimen and then increasing the dosage stepwise up to the dosage of the maintenance regimen.

Enumerated Embodiment 62: A method of treating an autoimmune disease in a patient having a co-morbidity susceptible to beta-blocker treatment comprising
a) administering to said patient an initial titration regimen of siponimod;
b) administering to said patient 1-15 mg siponimod daily as a maintenance regimen; and
c) introducing in said patient a beta-blocker treatment the earliest at the first day when said patient is receiving the dosage of the maintenance regimen;
wherein said initial titration regimen comprises administering siponimod at a dosage lower than the dosage of the maintenance regimen and then increasing the dosage stepwise up to the dosage of the maintenance regimen.

Enumerated Embodiment 63: A method of treating an autoimmune disease in a patient having a co-morbidity susceptible to beta-blocker treatment, receiving a chronic beta-blocker treatment and having a resting heart rate of >50 bpm under said chronic beta-blocker treatment comprising introducing in said patient a siponimod treatment by
a) administering to said patient art initial titration regimen of siponimod; and
b) administering to said patient 1-15 mg siponimod daily as a maintenance regimen;
wherein said initial titration regimen comprises administering siponimod at a dosage lower than the dosage used as a maintenance regimen and then increasing the dosage stepwise up to the dosage of the maintenance regimen.

Enumerated Embodiment 64: A method of treating an autoimmune disease in a patient having a co-morbidity susceptible to beta-blocker treatment, receiving a chronic beta-blocker treatment and having a resting heart rate of ≤50 bpm under said chronic beta-blocker treatment comprising
a) interrupting said chronic beta-blocker treatment in said patient until the baseline heart-rate is >50 bpm;
b) administering to said patient an initial titration regimen of siponimod; and initiating in said patient a siponimod treatment by
b1) administering to said patient an initial titration regimen of siponimod; and
b2) administering to said patient 1-15 mg siponimod daily as a maintenance regimen; and
c) re-initiating in said patient a beta-blocker treatment the earliest at the first day when said patient is receiving the dosage of the maintenance regimen;
wherein said initial titration regimen comprises administering siponimod at a dosage lower than the dosage used as a maintenance regimen and then increasing the dosage stepwise up to the dosage of the maintenance regimen.

Enumerated Embodiment 65: A method of combined administration of siponimod and a beta-blocker in a patient comprising
a) administering to said patient an initial titration regimen of siponimod;
b) administering to said patient 1-15 mg siponimod daily as a maintenance regimen; and c) introducing in said patient a beta-blocker treatment the earliest at the first day when said patient is receiving the dosage of the maintenance regimen;

wherein said initial titration regimen comprises administering siponimod at a dosage lower than the dosage of the maintenance regimen and then increasing the dosage stepwise up to the dosage of the maintenance regimen.

Enumerated Embodiment 66: A method of combined administration of siponimod and a beta-blocker in a patient receiving a chronic beta-blocker treatment and having a resting heart rate of >50 bpm under said chronic beta-blocker treatment comprising introducing in said patient a siponimod treatment by
a) administering to said patient an initial titration regimen of siponimod; and
b) administering to said patient 1-15 mg siponimod daily as a maintenance regimen;

wherein said initial titration regimen comprises administering siponimod at a dosage lower than the dosage used as a maintenance regimen and then increasing the dosage stepwise up to the dosage of the maintenance regimen.

Enumerated Embodiment 67: A method of combined administration of siponimod and a beta-blocker in a patient receiving a chronic beta-blocker treatment and having a resting heart rate of ≤50 bpm under said chronic beta-blocker treatment comprising
a) interrupting said chronic beta-blocker treatment in said patient until the baseline heart-rate is >50 bpm;
b) administering to said patient an initial titration regimen of siponimod; and initiating in said patient a siponimod treatment by
b1) administering to said patient an initial titration regimen of siponimod; and
b2) administering to said patient 1-15 mg siponimod daily as a maintenance regimen; and
c) re-initiating in said patient a beta-blocker treatment the earliest at the first day when said patient is receiving the dosage of the maintenance regimen;

wherein said initial titration regimen comprises administering siponimod at a dosage lower than the dosage used as a maintenance regimen and then increasing the dosage stepwise up to the dosage of the maintenance regimen.

Enumerated Embodiment 68: A method of co-administering siponimod and a beta-blocker in a patient comprising
a) administering to said patient an initial titration regimen of siponimod;
b) administering to said patient 1-15 mg siponimod daily as a maintenance regimen; and
c) introducing in said patient a beta-blocker treatment the earliest at the first day when said patient is receiving the dosage of the maintenance regimen;

wherein said initial titration regimen comprises administering siponimod at a dosage lower than the dosage of the maintenance regimen and then increasing the dosage stepwise up to the dosage of the maintenance regimen.

Enumerated Embodiment 69: A method of co-administering siponimod and a beta-blocker in a patient receiving a chronic beta-blocker treatment and having a resting heart rate of >50 bpm under said chronic beta-blocker treatment comprising introducing in said patient a siponimod treatment by
a) administering to said patient an initial titration regimen of siponimod; and
b) administering to said patient 1-15 mg siponimod daily as a maintenance regimen;

wherein said initial titration regimen comprises administering siponimod at a dosage lower than the dosage used as a maintenance regimen and then increasing the dosage stepwise up to the dosage of the maintenance regimen.

Enumerated Embodiment 70: A method of co-administering siponimod and a beta-blocker in a patient receiving a chronic beta-blocker treatment and having a resting heart rate of ≤50 bpm under said chronic beta-blocker treatment comprising
a) interrupting said chronic beta-blocker treatment in said patient until the baseline heart-rate is >50 bpm;
b) administering to said patient an initial titration regimen of siponimod; and initiating in said patient a siponimod treatment by
b1) administering to said patient an initial titration regimen of siponimod; and
b2) administering to said patient 1-15 mg siponimod daily as a maintenance regimen; and
c) re-initiating in said patient a beta-blocker treatment the earliest at the first day when said patient is receiving the dosage of the maintenance regimen;

wherein said initial titration regimen comprises administering siponimod at a dosage lower than the dosage used as a maintenance regimen and then increasing the dosage stepwise up to the dosage of the maintenance regimen.

Enumerated Embodiment 71: A method of treating an autoimmune disease in a patient comprising
a) administering to said patient an initial titration regimen of siponimod;
b) administering to said patient 1-15 mg siponimod daily as a maintenance regimen; and
c) introducing in said patient a beta-blocker treatment the earliest at the first day when a steady state of siponimod is reached;

wherein said initial titration regimen comprises administering siponimod at a dosage lower than the dosage of the maintenance regimen and then increasing the dosage stepwise up to the dosage of the maintenance regimen.

EXAMPLES

Example 1: Preparation of Immediate Release Tablets

For the titration/maintenance regimen, 0.25 mg, 0.5 mg, 1 mg and 2 mg siponimod immediate release film-coated tablets can be prepared as described below.

Process Blending:

In order to obtain a final mixture ready to be processed to a dosage form, e.g. a tablet, siponimod hemifumarate, e.g. having a X90 value of 18 μm, is blended with different excipients according to the flow diagram of FIG. 1. Therefore, siponimod hemifumarate is pre-blended in step 1 with a mixture of glyceryl behenate as moisture protective agent and spray-dried lactose as filler. The pre-blending is carried out in a diffusion mixer Bohle PM400S (L. B. Bohle Maschlnen+Verfahren GmbH, Ennlgerloh, Germany) for 10 min at 10 rpm. The mixture of step 1 is then sieved in step 2 using a screening mill having a mesh size of 800 μm. The sieved mixture is then blended in step 3 with further spray-dried lactose as filler, Aerosil as glidant, polyvinylpolypyrrolidon XL (crospovidone) as disintegrant and microcrystalline cellulose GR as filler in a diffusion mixer Bohle PM400S for 5 min at 10 rpm. The resulting mixture is again sieved in step 4 using an oscillating screening mill Frewitt GLA ORV having an mesh size of 800 Wand mixed in step 5 in a diffusion mixer Bohle PM400S for 25 min at 10 rpm.

In step 6 glyceryl behenate as lubricant, which has been sieved using an oscillating screening mill Frewitt GLA ORV having a mesh size of 800 μm, is added to the mixture of step 5 and mixed in step 7 in a diffusion mixer Bohle PM400S for 10 min at 10 rpm, resulting in the final dosage form mixture.

The final dosage mixture resulted from the blending process is then processed into a dosage form, preferably a tablet. The tablets are formed using a rotary tablet press, a Korsch PH 250 or Korsch XL400 with a compression force of 6 kN. The tablets are then de-dusted with a Krämer deduster (Krämer AG, Switzerland) and finally coated by a perforated pan coater Glatt Coater GC 750 (Glatt GmbH, Germany).

Instead of siponimod hemifumarate having a X90 value of 18 μm, siponimod hemifumarate of higher X90 values, e.g. 40-50 μm, or lower X90 values, e.g. 6 μm, can be used.

Film Coated Tablets:

Following the process of Example 1, film-coated tablets with the composition per tablet according to Tables 2 to 5 can be prepared.

TABLE 2

| Component | Composition per unit [%] | Composition per unit [mg/unit] |
| --- | --- | --- |
| Siponimod hemifumarate* (X90 = 18 μm) | 0.33 | 0.278 |
| Lactose - preblending step 1 | 7.32 | 6.220 |
| Lactose - step 3 | 65.85 | 55.977 |
| Total Lactose | 73.17 | 62.197 |
| Microcryst. cellulose | 15.0 | 12.750 |
| Polyvinylpolypyrrolidon XL | 6.0 | 5.100 |
| Aerosil 200 | 0.50 | 0.425 |
| Glyceryl behenate - step 1 | 2.0 | 1.7 |
| Glyceryl behenate - step 6 | 3.0 | 2.55 |
| Total Glyceryl behenate | 5.0 | 4.250 |
| Total core tablet | 100% | 85.000 mg |
| Coating premix | 5.134 | 4.6 |
| Total film coating tablet | 100% | 89.600 mg |

*The salt factor is 1.112

TABLE 3

| Component | Composition per unit [%] | Composition per unit [mg/unit] |
| --- | --- | --- |
| Siponimod hemifumarate* (X90 = 18 μm) | 0.65 | 0.556 |
| Lactose - preblending step 1 | 7.29 | 6.192 |
| Lactose - step 3 | 65.56 | 55.727 |
| Total Lactose | 72.85 | 61.919 |
| Microcryst. cellulose | 15.0 | 12.750 |
| Polyvinylpolypyrrolidon XL | 6.0 | 5.100 |
| Aerosil 200 | 0.50 | 0.425 |
| Glyceryl behenate - step 1 | 2.0 | 1.7 |
| Glyceryl behenate - step 6 | 3.0 | 2.55 |
| Total Glyceryl behenate | 5.0 | 4.250 |
| Total core tablet | 100% | 85.000 mg |
| Coating premix | 5.134 | 4.6 |
| Total film coating tablet | 100% | 89.600 mg |

*The salt factor is 1.112

TABLE 4

| Component | Composition per unit [%] | Composition per unit [mg/unit] |
| --- | --- | --- |
| Siponimod hemifumarate* (X90 = 18 μm) | 1.31 | 1.112 |
| Lactose - preblending step 1 | 7.22 | 6.136 |
| Lactose - step 3 | 64.97 | 55.227 |
| Total Lactose | 72.19 | 61.363 |
| Microcryst. cellulose | 15.0 | 12.750 |
| Polyvinylpolypyrrolidon XL | 6.0 | 5.100 |
| Aerosil 200 | 0.50 | 0.425 |
| Glyceryl behenate - step 1 | 2.0 | 1.7 |
| Glyceryl behenate - step 6 | 3.0 | 2.55 |
| Total Glyceryl behenate | 5.0 | 4.250 |
| Total core tablet | 100% | 85.000 mg |
| Coating premix | 5.134 | 4.6 |
| Total film coating tablet | 100% | 89.600 mg |

*The salt factor is 1.112

TABLE 5

| Component | Composition per unit [%] | Composition per unit [mg/unit] |
| --- | --- | --- |
| Siponimod hemifumarate* (X90 = 18 μm) | 2.62 | 2.224 |
| Lactose - preblending step 1 | 7.09 | 6.025 |
| Lactose - step 3 | 63.79 | 54.226 |
| Total Lactose | 70.88 | 60.251 |
| Microcryst. cellulose | 15.0 | 12.750 |
| Polyvinylpolypyrrolidon XL | 6.0 | 5.100 |
| Aerosil 200 | 0.50 | 0.425 |
| Glyceryl behenate - step 1 | 2.0 | 1.7 |
| Glyceryl behenate - step 6 | 3.0 | 2.55 |
| Total Glyceryl behenate | 5.0 | 4.250 |
| Total core tablet | 100% | 85.000 mg |
| Coating premix | 5.134 | 4.6 |
| Total film coating tablet | 100% | 89.600 mg |

*The salt factor is 1.112

Example 2: Clinical Trial

Participants

Healthy volunteers (men and women) aged between 18 and 55 years with a body mass index of 18-30 kg/m$^2$ were included in the study. Subjects were required to have an $FEV_1$ of ≥90% of predicted normal, a systolic blood pressure (BP) of 90-140 mm Hg, a diastolic BP of 50-90 mm Hg and a pulse rate of 50-90 bpm. Women of childbearing potential, pregnant or lactating women, homozygous carriers for CYP2C9*3 genotype, smokers, those with current or medical history of cardiovascular disorders or bronchospastic disease were excluded from this study. At screening, a 24 h Holter recording was performed on all subjects to exclude those with any significant arrhythmia.

Study Design

This was a double-blind, randomised, placebo-controlled study consisting of the following periods: screening (28 days), baseline evaluation (2 days), treatment (20 days) and study completion evaluation (approximately 10 days after the last drug administration; FIG. 1). Eligible subjects were domiciled for 22 days, starting approximately 36 h before dosing until 24 h post-dose after Day 20. The baseline evaluations were performed on Day −2 or Day −1. Subjects were randomised to one of the four treatment groups (A, B, C and D) in a ratio of 1:1:1:1. Subjects in Groups A and B received a combination of siponimod 2 mg once daily (qd) and propranolol 80 mg [long acting (LA)] qd, administered in two different sequences. In Group A, treatment was initiated with the siponimod dose-titration regimen (Days 1-6) followed by siponimod 2 mg (Days 7-20). Siponimod was uptitrated by one administration of 0.25 mg siponimod on day 1, one administration of 0.25 mg siponimod on day 2, one administration of 0.5 mg siponimod on day 3, one administration of 0.75 mg siponimod on day 4, one administration of 1.25 mg siponimod on day 5 and one administration of 2 mg siponimod on day 6, followed by a steady dose of 2 mg siponimod qd thereafter. Concomitantly, the subjects also received propranolol-placebo (Days 1-10) and propranolol 80 mg LA (Days 11-20). In Group B, the treatment was initiated with propranolol 80 mg LA and continued until Day 20. These subjects concomitantly received siponimod-placebo (Days 1-10), followed by the siponimod dose-titration regimen (Days 11-16) and siponimod 2 mg (Days 17-20). The subjects in Group C received siponimod-placebo and propranolol-placebo, whereas those in Group D received siponimod-placebo and propranolol 80 mg LA on all the treatment days. During the treatment phase, the subjects were required to fast (no food and liquid, except water) for at least 10 h before the administration of the study medication. Owing to the non-exact matching nature of propranolol-placebo, subjects were physically blinded with a sleeping mask at the time of dose administration. Post-dose, the subjects continued to fast for at least 1 h except on the days of PK sampling (Days 10 and 20) when the subjects fasted for 4 h.

Pharmacodynamic Assessments

The primary end point was the daily maximum effect on heart rate ($E_{max}$ HR) at steady state. The $E_{max}$ was defined as the maximum change from baseline in time matched, hourly average HR. A secondary end point was changes from baseline in average HR.

This study was designed to capture the treatment effects at the start, at the highest dose and at the pharmacokinetic steady state of siponimod dose titration. On the basis of previous reports (e.g. Legangneux et al, Br J Clin Pharmacol, 2013, 75, 831-841, and Murdoch et al, Br J Clin Pharmacol, 1991, 31, 323-332), it was deduced that it would take approximately 10 days for siponimod and 7 days for propranolol to reach a pharmacokinetic steady state in the study subjects. Accordingly, the cardiovascular effects were evaluated at baseline (−1) and on Days 1, 6 and 10, which correspond to the siponimod/propranolol monotherapy, and on Days 11, 16 and 20, which correspond to the combination treatment. Days 1 and 11 represented the initial dose of the siponimod titration regimen whereas Days 6 and 16 represented the highest dose and Days 10 and 20 represented the pharmacokinetic steady state.

The HR and bradyarrhythmias were evaluated from the 12-Lead Walter electrocardiogram (ECG) recordings. For HR, the evaluation interval began from the post-dose time or a corresponding time during the baseline (Day −1). The hourly average HR in each post-dose hour was calculated from the 60 intervals of per minute HR data. In order to calculate the time-matched change from baseline, each of the post-dose hourly average HR on a post-baseline evaluation day was subtracted from the corresponding hourly average HR at baseline.

The cardiac rhythm was evaluated from the 24 h post-dose Holter evaluation as mentioned earlier. AVBs of different degrees, SPs (>2 seconds) and any other arrhythmia were reported by the time of occurrence, duration and frequency.

Statistical Methods

The sample size was determined based on an inter-subject standard deviation (SD) of 5.6 bpm for $E_{max}$ HR from a previous study, derived from a fixed effects model. With 16 subjects in the propranolol alone arm (Group D) and in each of the combination treatment arms (Groups A and B), the difference in $E_{max}$ [half width of 90% confidence interval (CI)] was expected to be 2.82 bpm. This allowed a 90% CI completely <5 bpm, when the observed mean difference was approximately 2 bpm. Assuming a 15% drop-out, 76 subjects (19 per treatment arm) were randomised.

A mixed-effects ANCOVA model was used for analysing the pharmacodynamic end points. For the end points of HR, the model was applied on the $E_{max}$ data, with treatment, day and interaction of treatment and day as fixed factors, the average 24 h baseline HR as a covariate and subject as a random factor. An appropriate contrast was used to estimate the difference of treatment arms A and B combined versus the treatment arm D on Day 20. No imputation was done for missing values, as the derivation of the primary end point required both baseline and post-baseline data.

Subject Disposition and Demography

A total of 76 subjects were enrolled, and 73 subjects completed the study. The mean age (SD) of this study population was 37.1 (10.27) years, with a majority of subjects being males [n (%): 61 (80.3)] and Caucasian [45 (59.2%)]. The mean (SD) BMI of this population was 26.16 (2.57) kg/m².

Effect on Heart Rate

Effects on heart rate are shown in FIG. 2.

Analysis of the primary end point revealed that siponimod and propranolol alone led to a comparable $E_{max}$ HR. At Day 10, the mean $E_{max}$ HR was 16.79 bpm [standard error (SE): 1.61] for siponimod alone and 17.85 bpm (1.14) for propranolol alone (mean difference: −1.06 bpm; 95% CI: −4.98, 2.87; P=0.595) in comparison with 11.73 bpm (SE: 1.60) for placebo.

The actual additive effect of concomitant treatment of siponimod and propranolol was assessed at pharmacokinetic steady state of the combination (i.e. on Day 20). To measure the actual additive effect, Group A and Group B subjects were pooled (i.e. potential effects caused by the sequence of drug administration were fully randomized). The actual additive effect at pharmacokinetic steady state was an additional 6.21 bpm (95% CI: 2.32, 10.11; P=0.002) decrease in the mean $E_{max}$ HR versus propranolol alone.

Surprisingly, there was a significant effect caused by the sequence of drug administration. Whereas adding siponimod on top of propranolol led to a higher additional decrease in Emax HR versus propranolol alone, i.e. 7.39 bpm (95% CI: 2.87, 11.90; P=0.0016; Group B), adding propranolol on top of siponimod led to a much lower additional decrease, i.e. 5.04 bpm (95% CI: 0.52, 9.56; P=0.0292; Group A). This indicates that the sequence of drug administration is important and adding propranolol on top of siponimod has a better safety profile.

Said sequence effects were even more pronounced at the first day when the highest dose of siponimod was applied in Group B (i.e. 2 mg on Day 16): there the mean $E_{max}$ HR maximum in all Groups/days was observed. In Group B, the additional decrease was 10.24 bpm compared to 3.44 bpm in Group A.

Bradyarrhythmias

There were no episodes of second-degree AVBs or SPs of >3 seconds duration with siponimod alone or in combination with propranolol. Two episodes of Mobitz I AVB were reported during the propranolol only treatment. Sinus pauses (RR interval>2 seconds) were experienced by one subject in Group A (Days −1, 6, 11, 16 and 20) and two subjects in Group B (Day 16). None of these events were associated with clinical signs or symptoms.

The invention claimed is:

1. A method of treating an autoimmune disease in a patient comprising
   a) administering to said patient an initial titration regimen of siponimod;
   b) administering to said patient 1-15 mg siponimod daily as a maintenance regimen; and
   c) introducing in said patient a beta-blocker treatment the earliest at the first day when said patient is receiving the dosage of the maintenance regimen;
   wherein said initial titration regimen comprises administering siponimod at a dosage lower than the dosage of the maintenance regimen and then increasing the dosage stepwise up to the dosage of the maintenance regimen.

2. The method according to claim 1, wherein said autoimmune disease is selected from inflammatory myopathy and multiple sclerosis.

3. The method according to claim 1, wherein said autoimmune disease is selected from polymyositis, dermatomyositis, inclusion-body myositis and secondary progressive multiple sclerosis.

4. The method according to claim 1, wherein said autoimmune disease is secondary progressive multiple sclerosis.

5. The method according to claim 1, wherein the maintenance regimen administered in step b) of said method comprises 2-10 mg siponimod.

6. The method according to claim 5, wherein said maintenance regimen comprises 2-5 mg siponimod.

7. The method according to claim 1, wherein the maintenance regimen administered in step b) of said method is administered once daily.

8. The method according to claim 1, wherein in the maintenance regimen administered in step b) of said method an immediate release dosage form is used.

9. The method according to claim 1, wherein said initial titration regimen comprises administering siponimod such that the dosage administered on a specific day of the initial titration regimen is the sum of the dosages administered on the previous two days within a range of ±40%.

10. The method according to claim 1, wherein said initial titration regimen is conducted over 3-10 days.

11. The method according to claim 1, wherein the dosage of the maintenance regimen is 2 mg siponimod and wherein said initial titration regimen comprises administering 0.25 mg siponimod at day 1, 0.25 mg of siponimod at day 2, 0.5 mg siponimod at day 3, 0.75 mg siponimod at day 4, 1.25 mg siponimod at day 5 and 2 mg siponimod at day 6.

12. The method according to claim 11, wherein said initial titration regimen comprises one administration of 0.25 mg siponimod at day 1, one administration of 0.25 mg siponimod at day 2, one administration of 0.5 mg siponimod at day 3, one administration of 0.75 mg siponimod at day 4, one administration of 1.25 mg siponimod at day 5 and one administration of 2 mg siponimod at day 6.

13. The method according to claim 12, wherein, in said initial titration regimen, immediate release dosage forms comprising 0.25 mg, 0.5 mg, 1 mg and 2 mg siponimod are used.

14. The method according to claim 1,
   wherein said autoimmune disease is secondary progressive multiple sclerosis;
   wherein the maintenance regimen administered in step b) of said method is an immediate release dosage form comprising 2 mg siponimod;
   wherein the maintenance regimen administered in step b) of said method is administered once daily;
   wherein the initial titration regimen administered in step a) of said method comprises one administration of 0.25 mg siponimod at day 1, one administration of 0.25 mg siponimod at day 2, one administration of 0.5 mg siponimod at day 3, one administration of 0.75 mg siponimod at day 4, one administration of 1.25 mg siponimod at day 5 and one administration of 2 mg siponimod at day 6; and
   wherein in the initial titration regimen administered in step a) of said method immediate release dosage forms comprising 0.25 mg, 0.5 mg, 1 mg and 2 mg siponimod are used.

15. A method of treating an autoimmune disease in a patient receiving a chronic beta-blocker treatment and having a resting heart rate of >50 bpm under said chronic beta-blocker treatment comprising introducing in said patient a siponimod treatment by
   a) administering to said patient an initial titration regimen of siponimod; and
   b) administering to said patient 1-15 mg siponimod daily as a maintenance regimen;
   wherein said initial titration regimen comprises administering siponimod at a dosage lower than the dosage of the maintenance regimen and then increasing the dosage stepwise up to the dosage of the maintenance regimen.

16. The method according to claim 15, wherein said autoimmune disease is selected from inflammatory myopathy and multiple sclerosis.

17. The method according to claim 15, wherein said autoimmune disease is selected from polymyositis, dermatomyositis, inclusion-body myositis and secondary progressive multiple sclerosis.

18. The method according to claim 15, wherein said autoimmune disease is secondary progressive multiple sclerosis.

19. The method according to claim 15, wherein the maintenance regimen administered in step b) of said method comprises 2-10 mg siponimod.

20. The method according to claim 19, wherein said maintenance regimen comprises 2-5 mg siponimod.

21. The method according to claim 15, wherein the maintenance regimen administered in step b) of said method is administered once daily.

22. The method according to claim 15, wherein the maintenance regimen administered in step b) of said method is administered as an immediate release dosage form.

23. The method according to claim 15, wherein said initial titration regimen comprises administering siponimod such that the dosage administered on a specific day of the initial titration regimen is the sum of the dosages administered on the previous two days within a range of ±40%.

24. The method according to claim 15, wherein said initial titration regimen is conducted over 3-10 days.

25. The method according to claim 15, wherein the dosage of the maintenance regimen is 2 mg siponimod and wherein said initial titration regimen comprises administering 0.25 mg siponimod at day 1, 0.25 mg of siponimod at day 2, 0.5 mg siponimod at day 3, 0.75 mg siponimod at day 4, 1.25 mg siponimod at day 5 and 2 mg siponimod at day 6.

26. The method according to claim 25, wherein said initial titration regimen comprises one administration of 0.25 mg siponimod at day 1, one administration of 0.25 mg siponimod at day 2, one administration of 0.5 mg siponimod at day 3, one administration of 0.75 mg siponimod at day 4, one administration of 1.25 mg siponimod at day 5 and one administration of 2 mg siponimod at day 6.

27. The method according to claim 26, wherein, in said initial titration regimen, immediate release dosage forms comprising 0.25 mg, 0.5 mg, 1 mg and 2 mg siponimod are used.

28. The method according to claim 15,
wherein said autoimmune disease is secondary progressive multiple sclerosis;
wherein the maintenance regimen administered in step b) of said method is an immediate release dosage form comprising 2 mg siponimod;
wherein the maintenance regimen administered in step b) of said method is administered once daily;
wherein the initial titration regimen administered in step a) of said method comprises one administration of 0.25 mg siponimod at day 1, one administration of 0.25 mg siponimod at day 2, one administration of 0.5 mg siponimod at day 3, one administration of 0.75 mg siponimod at day 4, one administration of 1.25 mg siponimod at day 5 and; and one administration of 2 mg siponimod at day 6;
wherein in the initial titration regimen administered in step a) of said method immediate release dosage forms comprising 0.25 mg, 0.5 mg, 1 mg and 2 mg siponimod are used.

29. A method of treating an autoimmune disease in a patient receiving a chronic beta-blocker treatment and having a resting heart rate of ≤50 bpm under said chronic beta-blocker treatment comprising
a) interrupting said chronic beta-blocker treatment in said patient until the baseline heart-rate is >50 bpm;
b) initiating in said patient a siponimod treatment by
b1) administering to said patient an initial titration regimen of siponimod; and
b2) administering to said patient 1-15 mg siponimod daily as a maintenance regimen; and
c) re-initiating in said patient a beta-blocker treatment the earliest at the first day when said patient is receiving the dosage of the maintenance regimen;
wherein said initial titration regimen comprises administering siponimod at a dosage lower than the dosage of the maintenance regimen and then increasing the dosage stepwise up to the dosage of the maintenance regimen.

30. The method according to claim 29, wherein said autoimmune disease is selected from inflammatory myopathy and multiple sclerosis.

31. The method according to claim 29, wherein said autoimmune disease is selected from polymyositis, dermatomyositis, inclusion-body myositis and secondary progressive multiple sclerosis.

32. The method according to claim 29, wherein said autoimmune disease is secondary progressive multiple sclerosis.

33. The method according to claim 29, wherein the maintenance regimen administered in step b2) of said method comprises 2-10 mg siponimod.

34. The method according to claim 33, wherein said maintenance regimen comprises 2-5 mg siponimod.

35. The method according to claim 29, wherein the maintenance regimen administered in step b2) of said method is administered once daily.

36. The method according to claim 29, wherein the maintenance regimen administered in step b2) of said method is administered as an immediate release dosage form.

37. The method according to claim 29, wherein said initial titration regimen comprises administering siponimod such that the dosage administered on a specific day of the initial titration regimen is the sum of the dosages administered on the previous two days within a range of ±40%.

38. The method according to claim 29 wherein said initial titration regimen is conducted over 3-10 days.

39. The method according to claim 29, wherein the dosage of the maintenance regimen is 2 mg siponimod and wherein said initial titration regimen comprises administering 0.25 mg siponimod at day 1, 0.25 mg of siponimod at day 2, 0.5 mg siponimod at day 3, 0.75 mg siponimod at day 4, 1.25 mg siponimod at day 5 and 2 mg siponimod at day 6.

40. The method according to claim 39, wherein said initial titration regimen comprises one administration of 0.25 mg siponimod at day 1, one administration of 0.25 mg siponimod at day 2, one administration of 0.5 mg siponimod at day 3, one administration of 0.75 mg siponimod at day 4, one administration of 1.25 mg siponimod at day 5 and one administration of 2 mg siponimod at day 6.

41. The method according to claim 40, wherein, in said initial titration regimen, immediate release dosage forms comprising 0.25 mg, 0.5 mg, 1 mg and 2 mg siponimod are used.

42. The method according to claim 29, wherein the beta-blocker treatment re-initiated in step c) of said method is re-initiated after 2-3 weeks of treatment with siponimod.

43. The method according to claim 29,
wherein said autoimmune disease is secondary progressive multiple sclerosis;
wherein the maintenance regimen administered in step b2) of said method is an immediate release dosage form comprising 2 mg siponimod;
wherein the maintenance regimen administered in step b2) of said method is administered once daily;
wherein the initial titration regimen administered in step b1) of said method comprises one administration of 0.25 mg siponimod at day 1, one administration of 0.25 mg siponimod at day 2, one administration of 0.5 mg siponimod at day 3, one administration of 0.75 mg siponimod at day 4, one administration of 1.25 mg siponimod at day 5 and one administration of 2 mg siponimod at day 6;
wherein in the initial titration regimen administered in step b1) of said method immediate release dosage forms comprising 0.25 mg, 0.5 mg, 1 mg and 2 mg siponimod are used; and
wherein the beta-blocker treatment re-initiated in step c) of said method is re-initiated after 2 weeks of treatment with siponimod.

* * * * *

UNITED STATES PATENT AND TRADEMARK OFFICE
CERTIFICATE OF CORRECTION

| | | |
|---|---|---|
| PATENT NO. | : 11,944,602 B2 | Page 1 of 1 |
| APPLICATION NO. | : 17/209940 | |
| DATED | : April 2, 2024 | |
| INVENTOR(S) | : Eric Legangneux et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 59 days.

Signed and Sealed this
Tenth Day of June, 2025

Coke Morgan Stewart
*Acting Director of the United States Patent and Trademark Office*